US012806086B2

(12) United States Patent
Liu et al.

(10) Patent No.: US 12,806,086 B2
(45) Date of Patent: Nov. 24, 2026

(54) ABSORBENT ARTICLE WITH HYBRID NONWOVEN WEB

(71) Applicant: The Procter & Gamble Company, Cincinnati, OH (US)

(72) Inventors: Zhe Liu, Beijing (CN); Gueltekin Erdem, Beijing (CN); Lifeng Zhao, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 696 days.

(21) Appl. No.: 17/511,922

(22) Filed: Oct. 27, 2021

(65) Prior Publication Data

US 2022/0133553 A1 May 5, 2022

Related U.S. Application Data

(63) Continuation of application No. PCT/CN2020/125349, filed on Oct. 30, 2020.

(51) Int. Cl.
*A61F 13/514* (2006.01)
*A61F 13/15* (2006.01)
(Continued)

(52) U.S. Cl.
CPC .................. *A61F 13/51401* (2013.01); *A61F 13/15203* (2013.01); *A61F 13/51104* (2013.01);
(Continued)

(58) Field of Classification Search
CPC ........ A61F 13/5116; A61F 2013/51182; A61F 2013/51178; A61F 2013/51173;
(Continued)

(56) References Cited

U.S. PATENT DOCUMENTS 3,855,046 A 12/1974 Hansen et al.
5,885,267 A 3/1999 Mishima et al.
(Continued)

FOREIGN PATENT DOCUMENTS

CN 1350446 A 5/2002
CN 1530085 A 9/2004
(Continued)

OTHER PUBLICATIONS

PCT Supplementary Search Report and Written Opinion for PCT/CN2020/125349 dated Feb. 6, 2023, 8 pages.
(Continued)

*Primary Examiner* — Jacqueline F Stephens
*Assistant Examiner* — Seth Han
(74) *Attorney, Agent, or Firm* — Daniel S. Albrecht; Christian M. Best

(57) ABSTRACT

An absorbent article comprises a topsheet, a backsheet, and an absorbent core positioned between the topsheet and the backsheet. The absorbent article comprises a nonwoven web. The nonwoven web having a first side and a second side. The nonwoven web comprises thermoplastic fibers and cellulosic fibers. At least a portion of the thermoplastic fibers are present on the first side and at least a portion of the cellulosic fibers are present on the second side. The nonwoven web has a pattern of discrete bond points, wherein the pattern of discrete bond points has a fiber free-length parameter, as defined by the Fiber Free-Length Test, with a value of less than 2.90 mm. The second side of the nonwoven web forms part of an exterior surface of the absorbent article.

20 Claims, 12 Drawing Sheets

(51) Int. Cl.
*A61F 13/51* (2006.01)
*A61F 13/511* (2006.01)

(52) U.S. Cl.
CPC .................... *A61F 13/51121* (2013.01); *A61F 2013/15406* (2013.01); *A61F 2013/51004* (2013.01); *A61F 2013/51007* (2013.01); *A61F 2013/51019* (2013.01); *A61F 2013/51026* (2013.01); *A61F 2013/51028* (2013.01); *A61F 2013/5104* (2013.01); *A61F 2013/51061* (2013.01); *A61F 2013/51452* (2013.01)

(58) Field of Classification Search
CPC ............ A61F 2013/51169; A61F 2013/51165; A61F 13/5123; A61F 13/5125; A61F 13/512; A61F 13/5121; A61F 13/5122; A61F 13/5126; A61F 2013/5128; A61F 2013/5127; A61F 13/51121; A61F 2013/51139; A61F 2013/51019; A61F 13/51104; A61F 13/15731; B32B 5/022; B32B 2307/726; B32B 2555/02; B32B 5/26; B32B 27/12
See application file for complete search history.

(56) References Cited

U.S. PATENT DOCUMENTS

| | | | | |
|---|---|---|---|---|
| 10,646,381 | B2 | 5/2020 | Arora et al. | |
| 2007/0015428 | A1* | 1/2007 | Ishikawa | D04H 1/5418 442/415 |
| 2008/0026178 | A1 | 1/2008 | Stupperich et al. | |
| 2008/0176474 | A1 | 7/2008 | Brennan | |
| 2010/0310810 | A1 | 12/2010 | Bond et al. | |
| 2011/0319846 | A1* | 12/2011 | Rinnert | A61F 13/511 604/366 |
| 2012/0157950 | A1 | 6/2012 | Geilich et al. | |
| 2014/0127459 | A1* | 5/2014 | Xu | A61F 13/51121 428/141 |
| 2016/0242970 | A1 | 8/2016 | Qin et al. | |
| 2016/0262955 | A1 | 9/2016 | Kanya et al. | |
| 2017/0000663 | A1 | 1/2017 | Xu et al. | |
| 2017/0165396 | A1* | 6/2017 | Turner | A61F 13/514 |
| 2018/0133072 | A1* | 5/2018 | Uda | A61F 13/49 |
| 2019/0000696 | A1* | 1/2019 | Morishita | D04H 1/559 |
| 2019/0053958 | A1* | 2/2019 | Kurihara | A61F 13/53 |
| 2019/0071802 | A1 | 3/2019 | Novarino et al. | |
| 2019/0117473 | A1* | 4/2019 | Rosati | A61F 13/515 |
| 2019/0231612 | A1 | 8/2019 | Erdem et al. | |
| 2019/0374405 | A1 | 12/2019 | Giovanni et al. | |
| 2019/0380887 | A1 | 12/2019 | Ashraf et al. | |
| 2020/0248347 | A1 | 8/2020 | Novarino et al. | |

FOREIGN PATENT DOCUMENTS

| | | | |
|---|---|---|---|
| CN | 105228569 | A | 1/2016 |
| JP | 2005139594 | A | 6/2005 |
| JP | 2010269029 | A | 12/2010 |
| WO | 0033779 | A1 | 6/2000 |

OTHER PUBLICATIONS

PCT Search Report and Written Opinion for PCT/CN2020/125349 dated May 27, 2021, 12 pages.

* cited by examiner

ABSORBENT ARTICLE WITH HYBRID NONWOVEN WEB

CROSS REFERENCE TO RELATED APPLICATION

This application claims foreign priority under 35 U.S.C. § 119 to Chinese Patent Application No. PCT/CN2020/125349, filed on Oct. 30, 2020, which is herein incorporated by reference in its entirety.

FIELD

The present disclosure relates to nonwoven webs suitable for use in absorbent articles, and methods of forming such webs. In particular, it relates to an absorbent article including a nonwoven web comprising both thermoplastic fibers and cellulosic fibers. Such a nonwoven web may be suitable for use, in particular, in the topsheet, backsheet or belt of an absorbent article.

BACKGROUND

Absorbent articles, such as diapers, pants, adult incontinence pads, sanitary napkins and pantiliners, typically comprise a topsheet and a backsheet, with an absorbent core disposed between the topsheet and the backsheet. The topsheet and/or backsheet (and optionally other layers of the absorbent article) may comprise or consist of nonwoven webs.

It is desirable that nonwoven webs for use in absorbent articles are able to withstand the processing conditions in typical converting processes used in the manufacture of the absorbent articles, as well as typical in-use conditions.

The outer surface of a topsheet is desirably soft, for example, since it comes into contact with the skin of the wearer. The outer surface of a backsheet may also be provided by a nonwoven material. This can help to improve the perception of softness of the article. It may also help to create the impression of an article that is more like the woven fabric of an undergarment (compared with an article that has an exposed polymer film at the outer surface of the backsheet). Accordingly, a nonwoven for providing the outer surface of a backsheet is desirably also soft.

There is a need for absorbent articles containing improved nonwoven materials, which are robust to converting processes used in the manufacture of absorbent articles, as well as sufficiently robust to typical in-use conditions, and are themselves economical to manufacture, without compromising on the functional performance of either the nonwoven or the absorbent article as a whole, when in use.

Cotton offers a natural, skin-friendly material. However, compared with conventional synthetic materials used in nonwoven webs, it is relatively expensive, and the processes for forming it into a web may also be costly.

SUMMARY

It would be desirable to incorporate cotton (or other cellulosic fibers—in particular, natural cellulosic fibers) into an absorbent article; however, when doing this, it would desirable to use a basis weight of cellulosic fibers that is as low as possible, for reasons of cost and environmental sustainability. A low basis weight of cellulosic material may be especially desirable in a topsheet, because a low basis weight material can provide a dryness benefit compared with a high basis weight material. Less liquid may be trapped in the lower basis weight material, thereby reducing the likelihood of skin re-wet.

One way to produce a web with a low basis weight of cellulosic fibers is to combine the cellulosic fibers with thermoplastic fibers in a hybrid nonwoven web. Cellulosic fibers at a relatively low basis weight can be laid down on a pre-bonded thermoplastic nonwoven web, and the different fibers can be entangled using a spunlace (hydroentangling) process.

However, a problem can still arise at low basis weights, since the amount of cellulosic fiber may be insufficient to support strong entanglement. This problem manifests itself as poor abrasion resistance during use—the surface of the nonwoven tends to develop pilling or fuzz. In extreme cases, the loss of integrity of the fibrous web may present a safety risk to young babies.

The invention is defined by the claims. According to one aspect, there is disclosed an absorbent article comprising:

- a topsheet;
- a backsheet; and
- an absorbent core between the topsheet and the backsheet;
- wherein the absorbent article comprises a nonwoven web, the nonwoven web having a first side and a second side, the nonwoven web comprising thermoplastic fibers and cellulosic fibers;
- wherein at least a portion of the thermoplastic fibers are present on the first side and at least a portion of the cellulosic fibers are present on the second side;
- wherein the nonwoven web has a pattern of discrete bond points;
- wherein the pattern of discrete bond points has a fiber free-length parameter, as defined by the Free Fiber-Length Test herein, with a value of less than 2.90 mm; and
- wherein the second side of the nonwoven web forms part of an exterior surface of the absorbent article.

The inventors have surprisingly found that, by applying a suitable pattern of discrete bond points to the nonwoven web, the abrasion resistance can be improved and fuzz can be reduced even at relatively low basis weights of the cellulosic fiber.

The exterior (that is, outer) surface may be a body-facing surface or a garment facing surface. The absorbent article may be a diaper or pant, in particular.

The discrete bond points may be thermal bond points. At least some of the thermoplastic fibers may be fused together at the discrete bond points. At least some of the thermoplastic fibers may be fused onto at least some of the cellulosic fibers at the discrete bond points. At the bond points, fused thermoplastic fibers may form a fused mass of thermoplastic material. The fused mass of thermoplastic material may enrobe at least some of the cellulosic fibers.

The pattern of discrete bond points may be a 2-D pattern, comprising bond points spaced apart in each of two orthogonal dimensions. A 1-D pattern, such as a set of stripes that are spaced apart in one dimension but extend continuously in an orthogonal dimension, may result in a nonwoven material that is undesirably stiff.

The topsheet, the backsheet, the absorbent core, or another component of the absorbent article (such as a belt) may comprise the nonwoven web.

A majority of the fibers present on the first side may be provided by the thermoplastic fibers. A majority of the fibers present on the second side may be provided by the cellulosic fibers. The majority is determined by number of fibers. Here "majority" means a proportion greater than 50%.

The discrete bond points may be impressed into at least the first side of the nonwoven web. In some embodiments, the bond points may be impressed into both the first side and the second side.

The nonwoven web may be a spunlaced nonwoven web. A spunlaced nonwoven web may also be referred to as a hydroentangled nonwoven web.

The cellulosic fibers may be cotton fibers.

The cellulosic fibers may have a mean fiber length of at least 20 mm, wherein the mean fiber length is determined by weight of fibers according to the test method defined herein.

Independently of, or additionally to, any of the foregoing features, the cellulosic fibers may have a mean fiber length of less than or equal to 30 mm, wherein the mean fiber length is determined by weight of fibers according to the test method defined herein.

Several types of cotton may satisfy the mean fiber length range of 20 to 30 mm. For example, the cellulosic fibers may be US, Australian, or China Xinjiang cotton fibers.

Independently of, or additionally to, any of the foregoing features, the percentage of fibers that are shorter than 12.7 mm may be less than 35%, by weight of the fibers, measured according to the corresponding test method defined herein.

The nonwoven web may have a basis weight in the range 25-70 gsm. Optionally, the nonwoven web has a basis weight in the range 30-50 gsm.

The cellulosic fibers may be present in the nonwoven web at a basis weight in the range 10-50 gsm. For a sample of nonwoven web taken from a finished article, the basis weight of the cellulosic fibers can be determined by thermogravimetric analysis (TGA). The proportion of cellulosic fibers by weight of the web may be determined by TGA. The resulting value may be multiplied by the total basis weight of the web, to calculate the basis weight of the cellulosic fibers. Optionally, the cellulosic fibers are present in the nonwoven web at a basis weight in the range 10-25 gsm.

The thermoplastic fibers may be multicomponent fibers, comprising a first component and a second component, wherein the first component has a first melting point and the second component has a second melting point, and the first melting point is different from the second melting point. For a sample of nonwoven web taken from a finished article, the presence of multicomponent fibers, with components having different melting points, may be established by differential scanning calorimetry (DSC).

Optionally, the multicomponent fibers are bicomponent fibers. The bicomponent fibers may have a core-sheath structure, wherein one component forms the core and another component forms the sheath. The component forming the sheath preferably has the lower melting point.

The first component may be polyethylene. The second component may be polyethylene terephthalate (PET). In other examples, the first component may be a copolymer of polyethylene terephthalate (co-PET) and the second component may be PET. Other suitable combinations of first/second component include: polyethylene (PE)/polypropylene (PP); and PP/PET.

The pattern may be a regular pattern based on a primitive cell that repeats uniformly over the nonwoven web. The primitive cell may be defined by four lattice points, each lattice point located at the centroid of a respective one of the discrete bond points. In this case, the pattern is therefore defined by the lattice, with a lattice point at the centroid of each discrete bond point. The primitive cell may be a parallelogram, a rectangle, a square, or a rhombus.

The area of each discrete bond point may be less than 10 mm2, optionally less than 9 mm2, optionally less than 5 mm2, or less than 3 mm2 Independently of, or in addition to, any of the foregoing limitations, the area of each discrete bond point may be greater than 0.5 mm2 or greater than 2 mm2.

The discrete bond points may have at least one of, or any combination of two or more of: identical size; identical shape; and identical orientation.

The total area of the discrete bond points as a proportion of the total area of the nonwoven web may be in the range 5% to 50%, optionally 5% to 40%. Further optionally, the total area of the discrete bond points as a proportion of the total area of the nonwoven web may be in the range 8% to 40% or 20% to 40%.

The nonwoven web may form at least a part of the topsheet, and the second side of the nonwoven web may form a body facing surface of the absorbent article.

The nonwoven web may form at least a part of the backsheet, and the second side of the nonwoven web may form a garment facing surface of the absorbent article.

The absorbent article may further comprise a belt, wherein the nonwoven web forms at least a part of the belt.

A concentration of the thermoplastic fibers at the first side may be higher than a concentration of the cellulosic fibers at the first side, and/or a concentration of the thermoplastic fibers at the second side may be less than a concentration of the cellulosic fibers at the second side. These concentrations can be determined using TGA.

Optionally, the nonwoven web comprises apertures.

Optionally, the nonwoven web comprises projections and/or recesses. In this way, the nonwoven web may be provided with a three-dimensional texture.

The nonwoven web may be coated by a hydrophobic material. The fibers of the finished nonwoven web may be coated with a hydrophobic substance. This may improve the fluid handling and/or rewet properties of the nonwoven web, when used as a topsheet, for example. Suitable hydrophobic materials may include a triglyceride, diglyceride, monoglyceride, hydrocarbon, or a wax ester.

It will be understood that all of the features, values, and ranges disclosed above and in the claims are intended to be combined in any combination. This is true irrespective of whether the features are recited in the same sentence/claim/paragraph, or different claims/sentences/paragraphs. For example, in the case of a first claim to a range A, optionally a narrower range B, optionally a still narrower range C, for a first feature, and second claim to a range P, optionally a narrower range Q, optionally a still narrower range R, for a second feature, it will be understood that all combinations of {A or B or C} with {P or Q or R} are disclosed. In other words, in this example, the two claims give rise to a disclosure of nine combinations of ranges for the first feature and the second feature. All such combinations are to be understood as being disclosed.

BRIEF DESCRIPTION OF THE DRAWINGS

The invention will now be described by way of example with reference to the accompanying drawings, in which.

Figure 1:
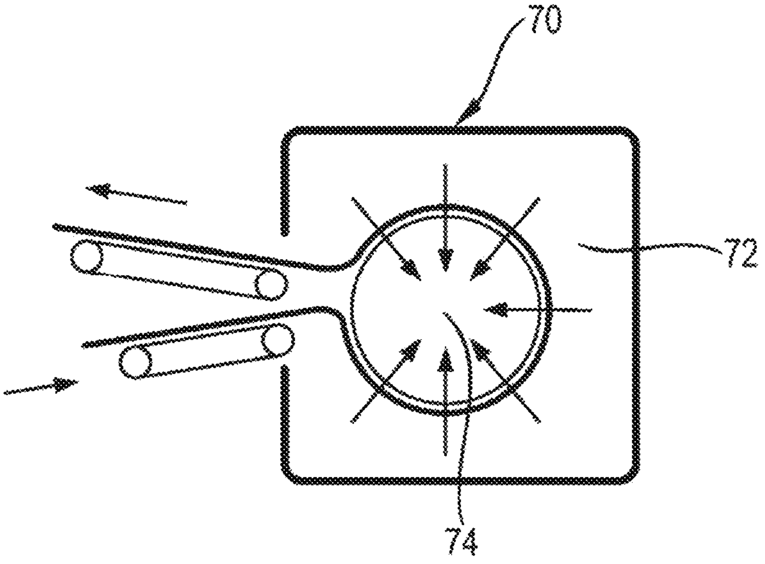
FIG. 1 is a schematic drawing illustrating a through air bonding process.
Figure 2:
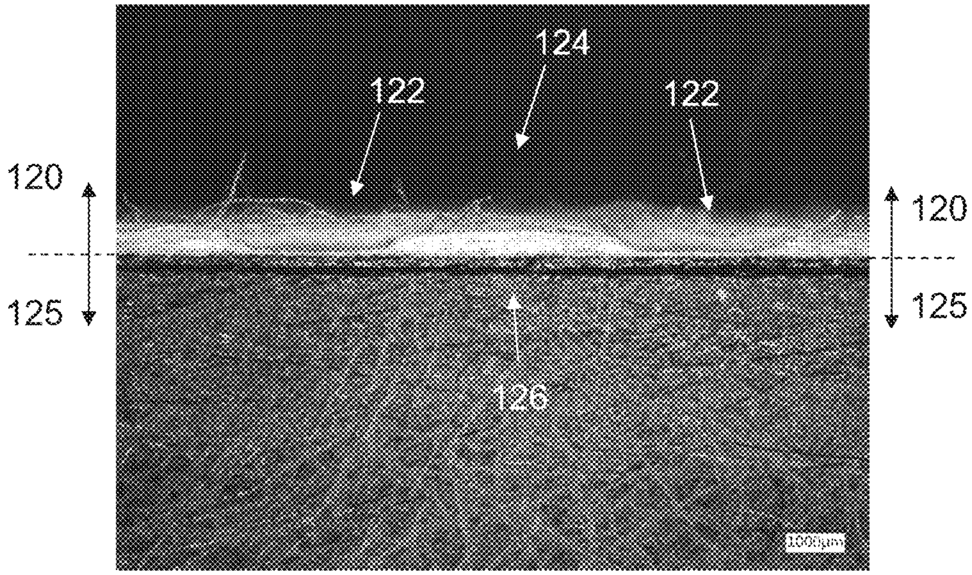
FIG. 2 is a micrograph showing a cross-sectional view of two adjacent bond points.
Figure 3:
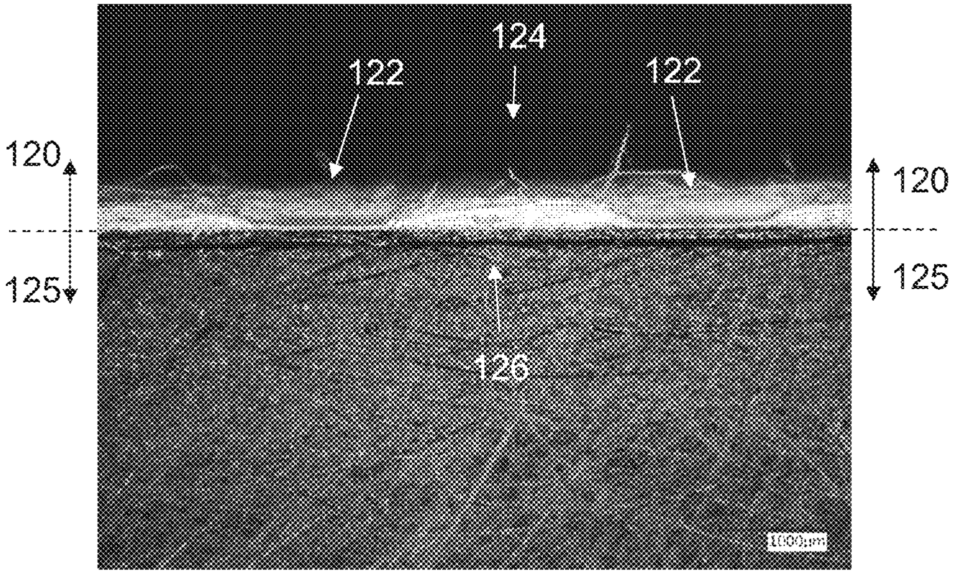
FIG. 3 is a micrograph showing another cross-sectional view of two adjacent bond points.
Figure 4:
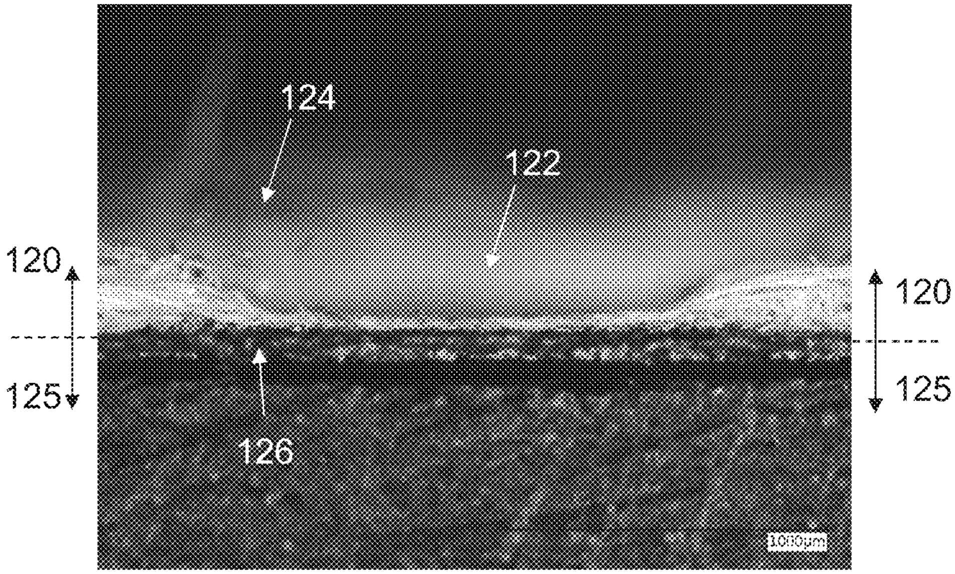
FIG. 4 is a micrograph showing an enlarged cross-sectional view of one bond point.
Figure 5:
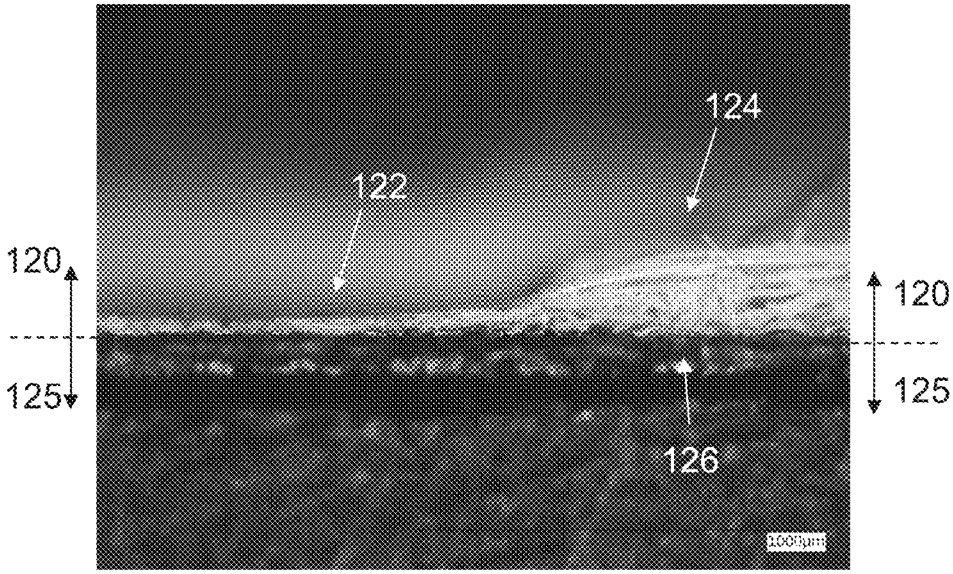
FIG. 5 is a micrograph showing an enlarged cross-sectional view of a bond point.
Figure 6:
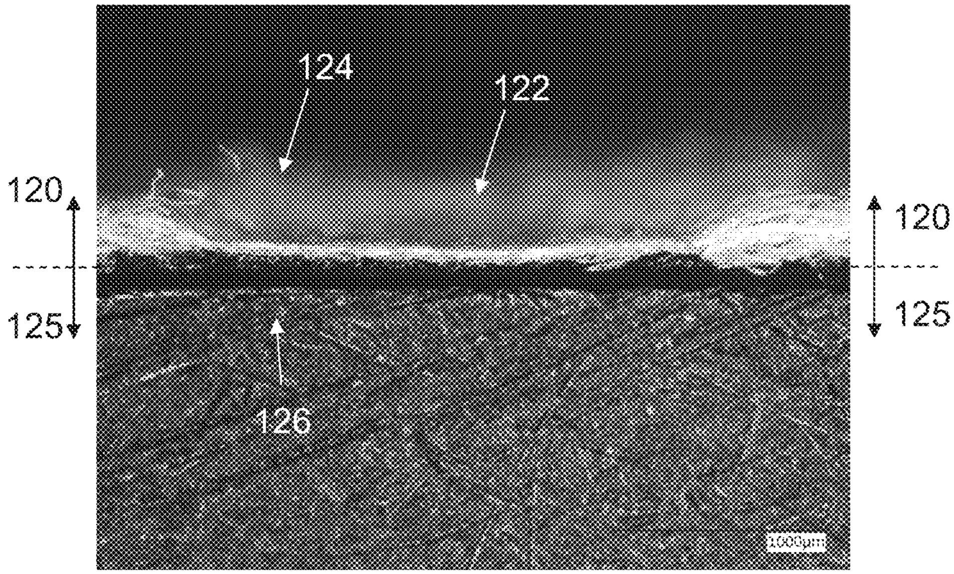
FIG. 6 is a micrograph showing a cross-sectional view of another bond point.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION OF THE INVENTION

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants, inserts, feminine care absorbent articles such as sanitary napkins or pantiliners, and the like. As used herein, the term "exudates" includes, but is not limited to, urine, blood, vaginal discharges, sweat and fecal matter. Preferred absorbent articles of the present invention are disposable absorbent articles, more preferably disposable diapers and disposable pants.

As used herein, the terms "autogenously bonding", "autogenously bonded" and "autogenous bond" refer to bonding between discrete fibers of a carded nonwoven web using through-air bonding. Autogenous bonding does not apply solid contact pressure such as is applied for point-bonding or calendaring processes and is done independently of externally added additives which promote or facilitate bonding, such as adhesives, solvents, and the like.

As used herein, "bicomponent" refers to fibers having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two subsections of the differing components of any shape or arrangement, including, for example, concentric core-and-sheath subsections, eccentric core/sheath subsections, side-by-side subsections, radial subsections, etc.

"Comprise," "comprising," and "comprises" are open ended terms; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "advantageously" and the like also qualify features that are not intended to limit the scope of the claims unless specifically indicated to do so.

As used herein, the term "machine direction" (or MD) is the direction parallel to the flow of a material through a manufacturing line. As used herein, the term "cross-machine direction" (or CD) is the direction perpendicular to the machine direction (or MD).

As used herein, "disposable" is used in its ordinary sense to mean an article that is disposed of or discarded after a limited number of usages over varying lengths of time, for example, fewer than 20 usages, fewer than 10 usages, fewer than 5 usages, or fewer than 2 usages. If the disposable absorbent article is a diaper, a pant, sanitary napkin, sanitary pad or wet wipe for personal hygiene use, the disposable absorbent article is most often intended to be disposed of after single use.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant maybe preformed anywhere along the circumference of the article (e.g., side fastened, front waist fastened). In a diaper, the waist opening and leg openings are only formed when the diaper is applied onto a wearer by (releasably) attaching the longitudinal edges of the first and second waist region to each other on both sides by a suitable fastening system.

As used herein, "monocomponent" refers to fiber formed of a single polymer component or single blend of polymer components, as distinguished from Bicomponent or Multicomponent fiber.

As used herein, "multicomponent" refers to fiber having a cross-section comprising two or more discrete polymer components, two or more discrete blends of polymer components, or at least one discrete polymer component and at least one discrete blend of polymer components. "Multicomponent fiber" includes, but is not limited to, "bicomponent fiber."

As used herein, the term "non-consolidated fibers" refers to fibers which are not formed into a self-sustaining, integral web.

As used herein, a "nonwoven web" is a manufactured web of directionally or randomly oriented fibers, consolidated and bonded together. The term does not include fabrics that are woven, knitted, or stitch-bonded with yarns or filaments. The basis weight of nonwoven webs is usually expressed in grams per square meter ($g/m^2$).

The term "web" as used herein means a material capable of being wound into a roll. Webs include but are not limited to nonwovens.

As used herein, the term "unit cell" means a unit that can be repeated, without rotation, gaps, or overlaps, to generate a regular lattice pattern. A lattice is an array of regularly spaced points. Although lattices and unit cells can be defined also in three dimensions, the present disclosure is concerned only with 2-D unit cells, generating 2-D lattice patterns.

As used herein, the term "primitive cell" refers to a unit cell having a lattice point at every vertex, and enclosing no other lattice points. In contrast, a non-primitive unit cell has one or more additional lattice points inside the unit cell. A primitive cell corresponds to a single lattice point, comprised of the partial lattice points enclosed at each of its vertices. For example, a square primitive cell encloses ¼ of a lattice point at each vertex. The same is true of a rectangular primitive cell. When the primitive cell is a parallelogram or a rhombus, the portion of the lattice point enclosed at each vertex will vary, depending on the angle characterizing the parallelogram or rhombus, but the sum of the portions will still be equal to one.

Unless otherwise specified, all dimensions and measurements specified herein are understood to be measured using the corresponding experimental procedures described in the "Test Methods" section of this document.

Embodiments of the invention relate to an absorbent article comprising a nonwoven web. The nonwoven web will be described first. Then, the absorbent article comprising the nonwoven web will be described.

Nonwoven Web

According to an example, a nonwoven web comprises thermoplastic fibers and cellulosic fibers. In the present example, the cellulosic fibers are cotton fibers.

The nonwoven web of this example is made by first forming a pre-bonded thermoplastic precursor nonwoven web. Cellulosic fibers (in particular, cotton fibers) are then laid down on this precursor nonwoven web. The cotton fibers and the thermoplastic precursor nonwoven web are hydroentangled, to create a spunlaced nonwoven web.

After the hydroentangling process, a pattern of discrete bond points is impressed into the spunlaced nonwoven web. In particular, the bond points are impressed into the side of the spunlaced nonwoven web corresponding to the thermoplastic precursor nonwoven web. That is, the bond points are impressed into the side opposite from side on which the cotton fibers were deposited.

Each of these components and steps will now be described in greater detail. (As will also be described further below, the method of making the nonwoven web may further include one or more optional additional stages—in particular, after the hydroentangling process.)

Carded Nonwoven Web

According to the present example, the thermoplastic precursor nonwoven web is a carded nonwoven web.

The carded nonwoven web comprises at least 50%, by weight of the carded nonwoven web, of staple fibers. In the presently described example, the nonwoven web comprises at least 95% by weight of the web of staple fibers, and preferably consists essentially of the staple fibers. The carded nonwoven web may, in addition to the staple fibers, consist of minor amounts of additives, such as odor control additives, perfumes, colored pigments or the like.

Staple fibers are short fibers. In the present example, the staple fibers have a mean length of 38 mm. The staple fibers are of substantially uniform length. It has been found that if the staple fibers are too short, they may detach from the cylinder during carding. On the other hand, if the staple fibers are too long, it may be difficult to transfer them off the cylinder.

The staple fibers laid down by the carding process form a layer of non-consolidated fibers. The layer then undergoes a through-air bonding process to form an autogenously bonded web. In the present example, the basis weight of the carded nonwoven web is 20 $g/m^2$ (20 gsm).

The carded, through air bonded web is a precursor web for a forming process to be described below.

Carding Process

Carding is a mechanical process using staple fibers. To obtain staple fibers, the fibers are first spun, cut to the required length, and put into bales (bundles of compressed fibers). The carding process starts with the opening of the bales of fibers. The fibers are typically conveyed to the next stage by air transport. They are then combed into a web by a carding machine, such as a rotating drum or series of drums covered in fine wires or teeth. The precise configuration of cards will depend on the fabric weight and fiber orientation required. The web can be parallel-laid, where most of the fibers are laid in the direction of the web travel, or they can be random-laid. Typical parallel-laid carded webs result in good tensile strength, low elongation and low tear strength in the machine direction and the reverse in the cross direction. A condenser roll may be provided after the carding cylinder, to generate some randomness of fiber orientation. The purpose of this condenser roll is to ensure a desired level of CD tensile strength.

In contrast to carded nonwoven webs, spunlaid and meltblown nonwoven webs are typically made in one continuous process. Fibers are spun and then directly dispersed into a web by deflectors or directed with air streams. The fibers of a spunlaid or meltblown nonwoven are considerably longer than staple fibers.

Through Air Bonding

As used herein, through-air bonding or "TAB" (also known as air through bonding or "ATB") means a process of bonding staple fibers of a layer of non-consolidated fibers, in which air is forced through the web, wherein the air is sufficiently hot to melt (or at least partly melt, or melt to a state where the fiber surface becomes sufficiently tacky) the polymer of a staple fiber or, if the staple fibers are multicomponent fibers, wherein the air is sufficiently hot to melt (or at least partly melt, or melt to a state where the fiber surface becomes sufficiently tacky) one of the polymers of which the fibers of the web are made. The air velocity is typically between 30 and 90 meter per minute and the dwell time may be as long as 6 seconds. The melting and resolidification of the polymer provides the bonding between different staple fibers.

A through air bonder is schematically shown in FIG. 1. In the through-air bonder 70, air having a temperature above the melting temperature of the polymer of the staple fiber (or, if the staple fibers are multicomponent fibers, above the melting temperature of a first fiber component and below the melting temperature of a second fiber component) is directed from the hood 72, through the web, and into the perforated roller 74. Alternatively, the through-air bonder may have a flat arrangement, wherein the air is directed vertically downward onto the web. The operating conditions of the two configurations are similar, the primary difference being the geometry of the web during bonding.

The hot air melts the staple fiber (or, for multicomponent fibers, the lower-melting polymer component) and thereby forms bonds between the staple fibers to consolidate and integrate the layer of staple fibers into a web.

As an example for a bicomponent fiber, when polypropylene and polyethylene are used as the polymer components, the air flowing through the through-air bonder usually has a temperature ranging from about 110° C. to about 162° C. at a velocity from about 30 to about 90 meters per minute. It should be understood, however, that the parameters of the through-air bonder depend on factors such as the type of polymers used and thickness of the fibrous layer.

The through-air bonding process forms the pre-bonded thermoplastic precursor nonwoven web of the present example.

Staple Fibers

As mentioned above, the carded nonwoven web comprises at least 50%, by weight of the carded nonwoven web, of staple fibers. In the presently described example, the web comprises at least 95% by weight of the web of the staple fibers.

Fibers useful for the carded nonwoven web according to the present disclosure include monocomponent fibers as well as multicomponent fibers. Multicomponent fibers are especially useful. Suitable multicomponent fibers are bicomponent fibers, such as core/sheath bicomponent fibers and side-by-side bicomponent fibers. The core/sheath bicomponent fibers maybe concentric or eccentric fibers.

The monocomponent or multicomponent fibers may be made of polymeric materials, such as polyolefins—for example, polypropylene (PP), or polyethylene (PE)—polyester, polyethylene terephthalate (PET), Co-PET, polybutylene terephthalate, polyamide, polylactic acid, viscose, and combinations thereof. The polymers may also comprise copolymers such as Co-PET. If the staple fibers comprise core/sheath bicomponent fibers, it is desirable that the sheath is made of a polymer which has a melting point below the melting point of the polymer which forms the core. If such bicomponent fibers are subjected to through-air bonding, the temperature of the through air bonding process is selected such that the polymer of the sheath is at least partially transferred to a molten state (or partly molten state, or molten to a state where the fiber surface becomes sufficiently tacky) such that the fibers bond together while the core of the bicomponent fiber remains substantially unaffected.

If side-by-side bicomponent fibers are used, the polymers forming the first and second component may also have different melting points. If such bicomponent fibers are subjected to through-air bonding, the temperature of the through air bonding process is selected such that the polymer of the component having the lower melting point is molten is at least partially transferred to a molten state (or to a state where the fiber surface becomes sufficiently tacky) such that the fibers bond together while the polymer of the component having the higher melting point remains substantially unaffected.

The carded nonwoven web may comprise a mixture of different types of fibers, such as a mixture of monocomponent fibers and bicomponent fibers. The staple fibers of the carded nonwoven web may comprise at least 20%, or at least 35%, or at least 50%, or at least 60%, or at least 70%, or at least 80%, by total weight of the staple fibers, of multicomponent fibers, such as core/sheath or side-by-side bicomponent fibers. The staple fibers may also consist only of multicomponent fibers, such as bicomponent fibers. The staple fibers may be a mixture of different multicomponent fibers, e.g. a mixture of different bicomponent fibers.

In the presently described example, the staple fibers consist essentially of bicomponent fibers. In particular, the staple fibers consist essentially of core/sheath bicomponent fibers, with a core formed of polyethylene terephthalate and a sheath formed of polyethylene.

In other examples, the carded nonwoven web may also comprise monocomponent fibers. For example, the staple fibers may comprise at least 5%, or at least 10%, or at least 15%, or at least 20%, or at least 25%, by total weight of the staple fibers, of monocomponent fibers. The carded nonwoven web may comprise at most 50%, or at most 40%, or at most 30%, by total weight of the staple fibers, of monocomponent fibers.

The staple fibers of the carded nonwoven web may consist of a mixture of bicomponent fibers (such as core/sheath bicomponent fibers or side-by-side bicomponent fibers) and monocomponent fibers, such that the bicomponent fibers and the monocomponent fibers together form 100% of the total weight of the staple fibers.

The shape of the staple fibers of the carded nonwoven web may be round (i.e. fibers having a circular cross-section). Alternatively, the staple fibers may have non-round shape, such as multilobal fibers (e.g. trilobal fibers), flat fibers ("ribbon-like" cross-section), rhomboid fibers, or triangular fibers. In multilobal fibers, a central section is encircled by a multiplicity of lobes. E.g. in a trilobal fiber, the central section is encircled by three lobes.

The staple fibers may comprise or consist of a mixture of solid, round bicomponent fibers (such as core/sheath or side-by-side bicomponent fibers) and solid, multilobal (such as trilobal) monocomponent fibers. Alternatively, the staple fibers may comprise or consist of a mixture of solid, round bicomponent fibers (such as core/sheath or side-by-side bicomponent fibers) and solid, round monocomponent fibers.

In the presently described example, the PET/PE core/sheath fibers consist essentially of round fibers. They have a linear density of 2.2 dtex (2 denier). It was found that the fiber denier was substantially unchanged by the forming process (described below); therefore, both the precursor web and the final nonwoven web exhibit substantially the same fiber denier.

To make a nonwoven web by carding and through air bonding it is preferable that the staple fibers have crimp. This facilitates the carding step, in particular. In some examples, a certain percentage of non-crimped fibers can be blended with the crimped fibers; however, a high level of non-crimped fibers may cause process failures, such as cylinder blocking. Preferably, the nonwoven web comprises at least 95% by weight of the nonwoven web of crimped fibers. In the presently described example, the nonwoven web consists essentially of crimped fibers. That is, the PET/PE core/sheath fibers are crimped bicomponent fibers. The fibers have a crimp number in the range 13 to 17 per 2.5 cm (13 to 17 per inch).

In the present example, the thermoplastic fibers are treated with a hydrophilic coating. This can help with wetting of the thermoplastic fibers in the subsequent hydroentangling process (see below). The hydrophilic coating may be washed off during the hydroentangling process, such that it is not detectable in the final product.

Cotton Fibers

The pre-bonded thermoplastic precursor nonwoven web, produced in the through air bonding process, is used as a substrate, on which cotton fibers are deposited.

In the examples listed in Table 1 below, 10 to 25 gsm of cotton fibers are laid down on the thermoplastic precursor nonwoven web. The through-air bonded precursor web (formed of 20 gsm, 2 denier PE/PET hydrophilic coated fibers) is unwound on the conveying belt of a carding line. The cotton fibers are laid down on top of the TAB nonwoven with a target basis weight.

In the present example, the cotton fibers have a mean fiber length in the range 20 to 30 mm Such fibers may be provided by US, Australian, or China Xinjiang cotton.

The total basis weight of the nonwoven web, including the thermoplastic and cotton fibers may be in the range 25-70 gsm, optionally 30-50 gsm.

The side of the thermoplastic precursor nonwoven web that faces away from the cotton corresponds to a first side 124 of the finished nonwoven web. This is the underside of the thermoplastic precursor nonwoven web, when the cotton is laid on top of the precursor web. The side on which the cotton is laid corresponds to a second side 126 of the finished nonwoven web. Note that, although the cotton fibers are initially laid on top of the thermoplastic precursor nonwoven web, the cotton fibers might not form a distinct layer in the finished nonwoven web, because of the hydroentangling process that follows.

Hydroentangling

The cotton fibers are entangled with the thermoplastic fibers of the precursor nonwoven web, by hydroentangling. This forms a spunlaced nonwoven web comprising a mixture of entangled thermoplastic and cellulosic fibers.

To perform the hydroentangling, the thermoplastic precursor nonwoven web with the cotton fibers deposited on top is conveyed into a spunlace unit. Here, the cotton fibers are entangled with the through-air bonded fibers of the thermoplastic precursor nonwoven web, by means of water jets, to form a spunlaced nonwoven web. By suitably controlling the pressure of the water jets, the cotton fibers are redistributed through the thickness of the thermoplastic precursor nonwoven web. This forms a concentration distribution through the thickness of the spunlaced nonwoven web, wherein the top side (second side 126) contains a greater concentration of cotton fibers than the bottom side (first side 124).

To a large extent, the original bonding structure of the thermoplastic precursor nonwoven web, imparted previously by the through-air bonding, is not broken by the water jets. (The individual fiber-to-fiber bonds between the thermoplastic fibers may still be detected in the finished nonwoven web, by viewing it under a microscope.)

After the hydroentangling by the water jets, the spunlaced nonwoven web is conveyed to the nip between a pair of squeezing rolls, to dewater the web. From there, the spunlaced nonwoven web passes through an oven, for drying.

Pattern of Bond Points

After drying, a pattern of bond points is imparted to the spunlaced nonwoven web. In the present example, this is done by passing the spunlaced nonwoven web through the nip of a pair of heated calender rolls. The pair of rolls consists of a pin roll and a smooth roll. The first side of the spunlaced nonwoven web faces the pin roll. The second side of the spunlaced nonwoven web faces the smooth roll. Since the first side is relatively richer in thermoplastic fibers, and the second side is relatively richer in cotton fibers, this means that the side that is rich in thermoplastic fibers faces the pin roll.

The temperature of the pin roll is higher than the temperature of the smooth roll. As will be understood by those skilled in the art, the specific temperature settings may be chosen depending on the speed at which the spunlaced web passes between the calender rolls. In the present example, the speed is about 30 m/min (0.5 m/s). The temperature of the pin-roll is about 120° C. to about 140° C., and the temperature of the smooth roll is about 90° C. to about 110° C. These temperatures (and this speed) were found to be suitable for a spunlaced web with the properties described above (a thermoplastic precursor nonwoven web formed of PE/PET bicomponent fibers at a basis weight of 20 gsm, and cotton fibers at a basis weight of 10 to 25 gsm).

In the nip between the calender rolls, discrete bond points are impressed into the first side of the spunlaced nonwoven web by the pins of the pin roll. Each pin imparts (impresses) one bond point into the web. Each bond point comprises a depression in the first surface of the spunlaced nonwoven web.

At the bond points, the first side 124 of the spunlaced nonwoven web (which is rich in thermoplastic fibers) is compressed towards the second side 126 of the web (which is rich in cotton fibers). At least one component of the thermoplastic fibers in the precursor nonwoven web is at least partially melted, under the heat and pressure applied by each pin. Without wishing to be bound by theory, in the present example, it is believed that the component of the bicomponent fibers having the lower melting point is at least partially melted at the tips of the pins. (In the present example, this is the PE component.) The at least partially melted component flows around some of the cotton fibers, enrobing these cotton fibers and securing them at the resulting bond point.

FIG. 2-6 show cross-sectional microscopic views of bond points 122 according to an example. To capture these images, the finished nonwoven web 120 was attached to a support 125. Then, both the nonwoven web 120 and support 125 were cut, to open up a cross-section of the nonwoven web 120. In the images, the dashed horizontal lines delineate the boundary between the nonwoven web 120 and the support 125. The upper side of the nonwoven web in these images is the first side 124—that is, the side of the nonwoven web that is rich in thermoplastic fibers. The lower side of the nonwoven web in these images is the second side 126—that is, the side of the nonwoven web that is rich in cotton fibers.

Figure 7:
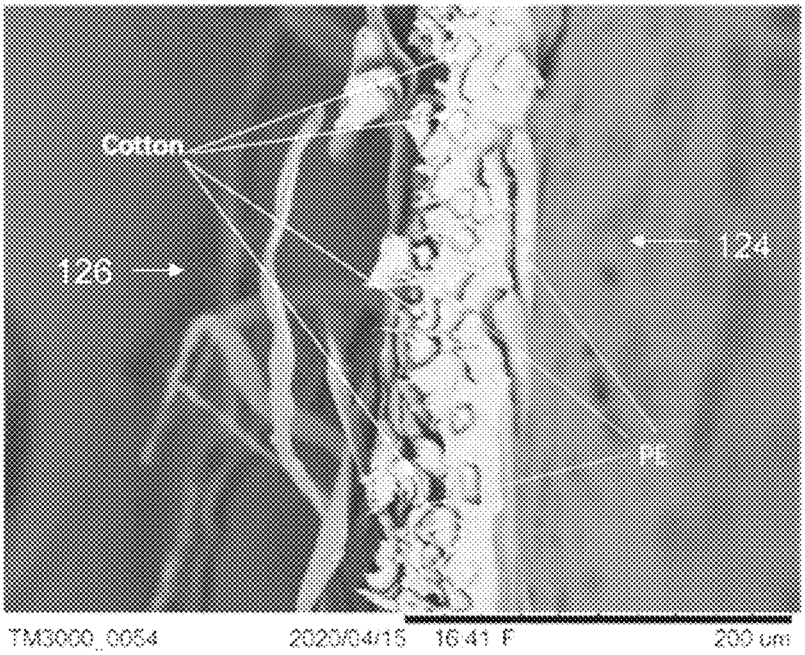
FIG. 7 is a scanning electron microscope image of a bond point, in a cross-sectional view.

FIG. 7 is a scanning electron microscope (SEM) image showing a cross-sectional view of part of a bond point. Here, it can be seen that the PE component has melted and flowed around the individual cotton fibers in the web.

Figure 8:
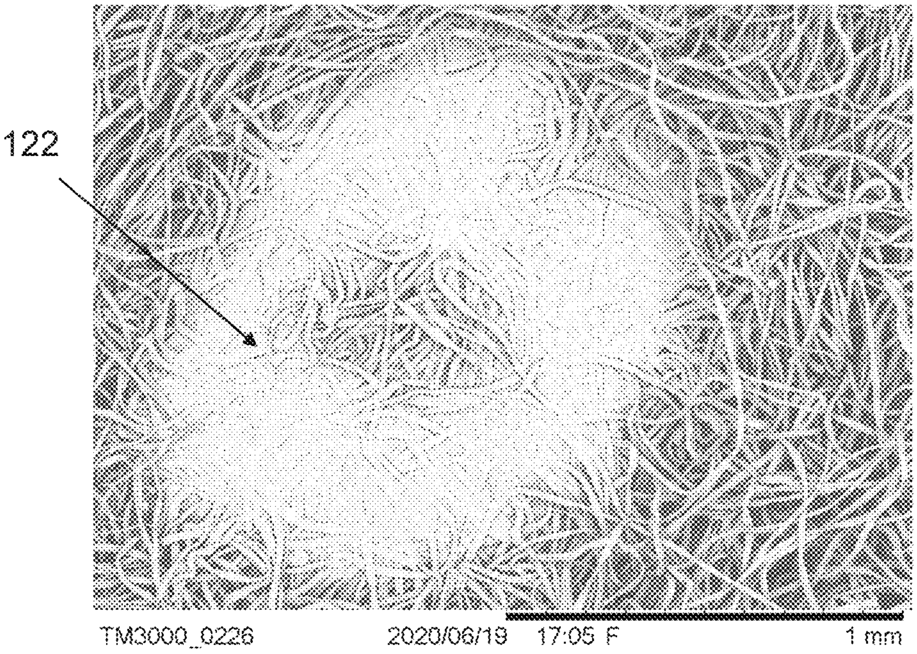
FIG. 8 is scanning electron microscope image of a bond point, in plan view.
Figure 9:
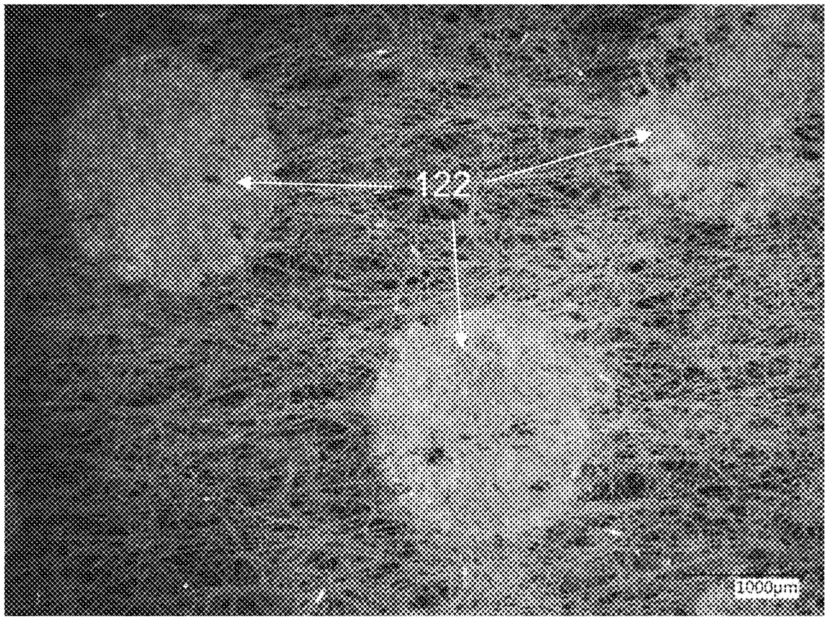
FIG. 9 is a micrograph showing several circular bond points.

Each bond point has a shape, in plan view, corresponding to the shape of the head of the pin that created it. FIG. 8 is an SEM image showing a plan view of a bond point according to an example. The bond point is circular in shape. Again, it can be seen how the PE component flows around the cotton fibers, enrobing and immobilizing them, as a result of the melting of the PE component at the bond point. The cotton fibers are embedded in the PE component. At least some of the thermoplastic fibers may be fused together, into a mass of thermoplastic material, at the bond points. The fused mass of thermoplastic material may enrobe and immobilize the cotton fibers. FIG. 9 is a microscopic image showing three bond points 122. This image was taken from the first side 124 of the nonwoven web (that is, the side rich in thermoplastic fibers). Again, the bond points shown in this example are circular.

In the present example, the second surface of the nonwoven web remains substantially flat after formation of the bond points. (The second surface faces the smooth roll, when the spunlaced web passes through the nip of the calender rolls.)

Figure 10A:
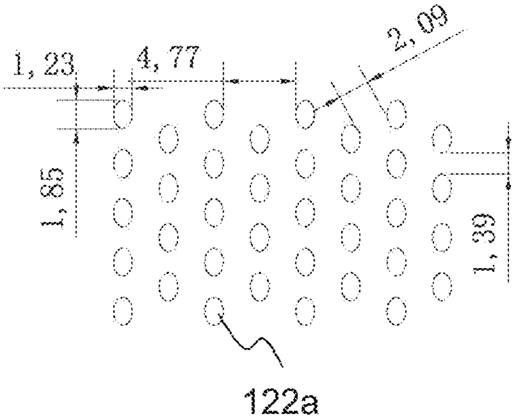
FIGS. 10A-H show examples of different patterns of bond points.
Figure 10B:
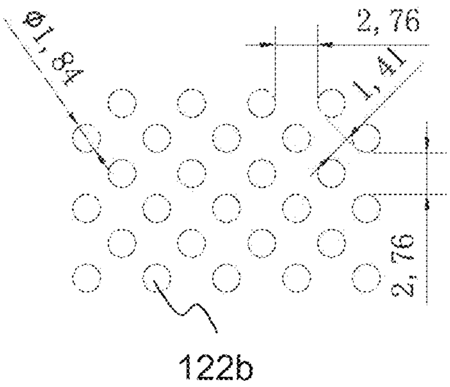
Figure 10C:
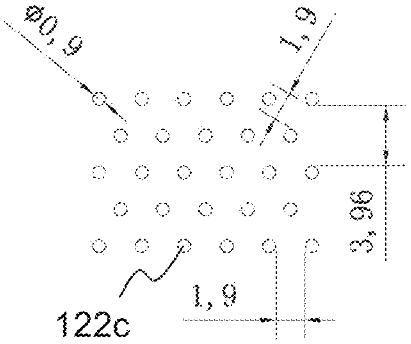
Figure 10D:
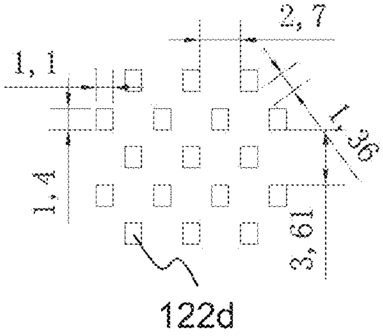
Figure 10E:
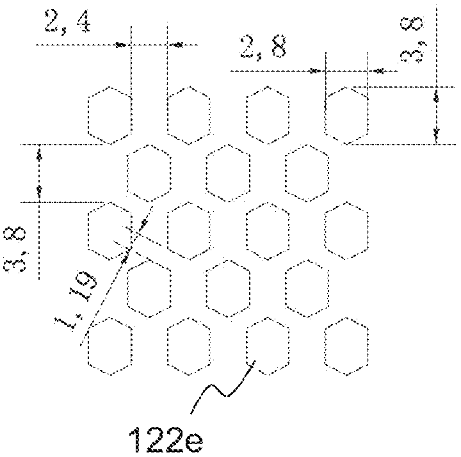
Figure 10F:
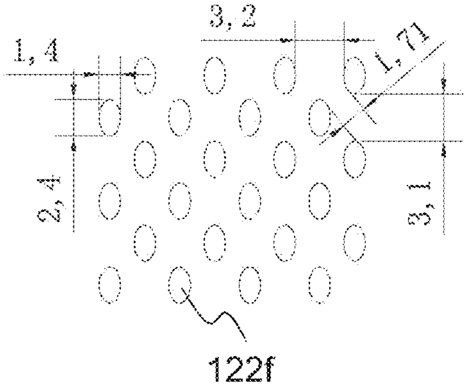
Figure 10G:
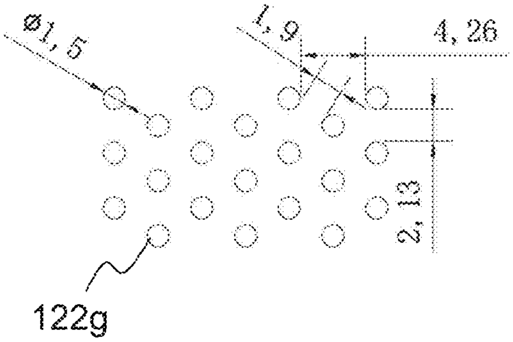
Figure 10H:
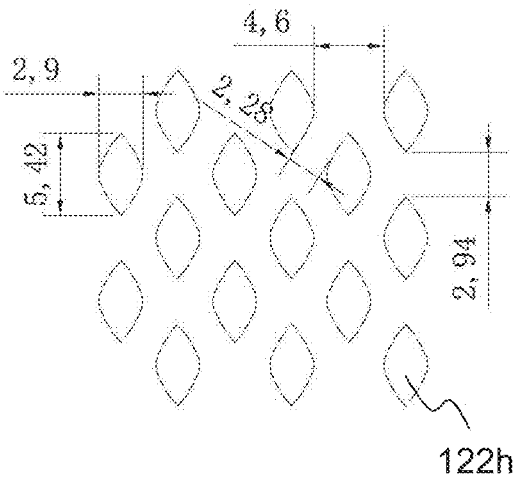

FIGS. 10A-10H show examples of patterns of bond points. In these examples, the pattern defines a regular lattice. Each of these patterns has a primitive cell that is a rhombus. In FIG. 10A, the bond points 122*a* are elliptical; in FIG. 10B, the bond points 122*b* are circular; and in FIG. 10C, the bond points 122*c* are circular, with a smaller size than the bond points 122*b* of FIG. 10B. In FIG. 10D, the bond points 122*d* are rectangular; in FIG. 10E, the bond points 122*e* are hexagonal; and in FIG. 10F, the bond points 122*f* are elliptical, with a larger size than the bond points 122*a* in FIG. 10A. In FIG. 10G, the bond points 122*g* are circular, with an intermediate size, between that of bond points 122*b* and 122*c*. In FIG. 10H, the bond points 122*h* are lozenge-shaped. It will be appreciated that the pattern of bond points need not necessarily define a regular lattice, although this may be preferred for uniformity of the resulting web.

In the examples illustrated in FIGS. 10A-H, the bond points in each pattern have identical size, shape, and orientation. The total area of the discrete bond points as a proportion of the total area of the nonwoven web bearing the pattern is in the range 5% to 50%, optionally 5% to 40%, further optionally, 20% to 40%.

Additional Features

Optionally, the spunlaced nonwoven web, having the pattern of thermal bond points imparted to it, may be processed further after the thermal bonding step. For example, a hydrophobic wax may be applied to the web. Alternatively or in addition, the nonwoven material may be further processed to form 3D textures or apertures. 3D textures and and/or apertures may provide improved fluid handling properties, for example, if the nonwoven web is used as (or in) a topsheet. A 3D texture may comprise projections and/or recesses. For example, the nonwoven web may be embossed so that it comprises projections on one surface of the nonwoven web and corresponding recesses on the opposite surface.

EXAMPLES

Experiments were carried out with various nonwoven webs, made as described above. These differed in the fiber composition of the webs and in the bonding pattern imparted to them. The pattern of bond points can be characterized by the fiber free-length parameter, measured according to the procedure defined in the test methods section, herein. For each example, the resistance of the nonwoven web to abrasion was evaluated. The fuzz resistance is characterized using a fuzz score. This is measured according to the corresponding procedure defined in the test methods section, herein.

The webs of the examples in Table 1 below were made using the following process. An air-through-bonded (ATB) nonwoven (20 gsm, 2 denier PE/PET hydrophilic coated fibers) was unwound on the conveying belt of a carding line. Cotton fibers were laid down on top of the ATB nonwoven with a target basis weight (see Table 1). Then, the web was conveyed into a spunlace unit, where the cotton fibers were entangled with the ATB nonwoven fibers by water jets. The pressure of the water jets was controlled so that the cotton fibers formed a concentration distribution through the thickness of ATB nonwoven, with the top side containing a higher concentration of cotton fibers than the bottom side. The original bonding structure of the ATB nonwoven was not broken by the water jets. After hydroentangling, the nonwoven web was nipped by a pair of squeezing rolls and taken through an oven for drying. After drying, the nonwoven material had bond points impressed into it by a pair of heated calender rolls—namely, a pin roll, and a smaller, smooth roll. The side of the nonwoven with the higher concentration of cotton fibers (second side 126) faced the smooth roll, and the side the lower concentration of cotton fibers (first side 124) faced the pin roll. The temperature of the pin roll was higher than that of the smooth roll. In particular, the speed through the nip of the calender rolls was about 30 m/min, the temperature of the pin-roll was about 120-140° C., and the temperature of the smooth roll was about 90-110° C.

TABLE 1

| Examples | | | | | | | | | | |
|---|---|---|---|---|---|---|---|---|---|---|
| No. | Bond pattern (FIG. #) | Side facing pin roll | Cotton/ ATB (gsm) | Bond point area ($mm^2$) | % bonded area | $D_{MD}$ (mm) | $D_{CD}$ (mm) | $D_{AV}$ (mm) | Fuzz score | A/L (mm) |
| 1 | 10E | ATB side | 15 gsm/ 20 gsm | 8.61 | 43.5% | 3.8 | 2.4 | 3.02 | 1 | 2.67 |
| 2 | 10A | ATB side | 15 gsm/ 20 gsm | 1.79 | 18.3% | 1.39 | 4.77 | 2.57 | 1 | 1.66 |
| 3 | 10B | ATB side | 15 gsm/ 20 gsm | 2.66 | 25.1% | 2.76 | 2.76 | 2.76 | 1 | 2.87 |
| 4 | 10C | ATB side | 15 gsm/ 20 gsm | 0.64 | 9.3% | 3.96 | 1.9 | 2.74 | 2 | 1.56 |
| 5 | 10G | ATB side | 15 gsm/ 20 gsm | 1.77 | 16.9% | 2.13 | 4.26 | 3.01 | 2 | 2.04 |
| 6 | 10H | ATB side | 15 gsm/ 20 gsm | 9.90 | 31.5% | 2.94 | 4.6 | 3.68 | 4 | 4.66 |
| 7 | 10D | ATB side | 15 gsm/ 20 gsm | 1.54 | 16.1% | 3.61 | 2.7 | 3.12 | 4 | 2.96 |
| 8 | 10F | ATB side | 15 gsm/ 20 gsm | 2.64 | 20.8% | 3.1 | 3.2 | 3.15 | 4 | 3.13 |
| 9 | None | None | 15 gsm/ 20 gsm | 0 | 0.0% | NA | NA | NA | 5 | NA |
| 10 | 10A | Cotton side | 15 gsm/ 20 gsm | 1.79 | 18.3% | 1.39 | 4.77 | 2.57 | 4 | 1.66 |
| 11 | 10B | Cotton side | 15gsm/ 20 gsm | 2.66 | 25.1% | 2.76 | 2.76 | 2.76 | 4 | 2.87 |

TABLE 1-continued

| | | | | | | | | | | |
|---|---|---|---|---|---|---|---|---|---|---|
| Examples | | | | | | | | | | |
| No. | Bond pattern (FIG. #) | Side facing pin roll | Cotton/ ATB (gsm) | Bond point area ($mm^2$) | % bonded area | $D_{MD}$ (mm) | $D_{CD}$ (mm) | $D_{AV}$ (mm) | Fuzz score | A/L (mm) |
| 12 | 10C | Cotton side | 15 gsm/ 20 gsm | 0.64 | 9.3% | 3.96 | 1.9 | 2.74 | 5 | 1.56 |
| 13 | 10E | ATB side | 25 gsm/ 20 gsm | 8.61 | 43.5% | 3.8 | 2.4 | 3.02 | 1 | 2.67 |
| 14 | 10A | ATB side | 25 gsm/ 20 gsm | 1.79 | 18.3% | 1.39 | 4.77 | 2.57 | 1 | 1.66 |
| 15 | 10B | ATB side | 25 gsm/ 20 gsm | 2.66 | 25.1% | 2.76 | 2.76 | 2.76 | 1 | 2.87 |
| 16 | 10H | ATB side | 25 gsm/ 20 gsm | 9.90 | 31.5% | 2.94 | 4.6 | 3.68 | 3 | 4.66 |
| 17 | 10D | ATB side | 25 gsm/ 20 gsm | 1.54 | 16.1% | 3.61 | 2.7 | 3.12 | 3 | 2.96 |
| 18 | 10F | ATB side | 25 gsm/ 20 gsm | 2.64 | 20.8% | 3.1 | 3.2 | 3.15 | 3 | 3.13 |
| 19 | None | None | 25 gsm/ 20 gsm | 0 | 0.0% | NA | NA | NA | 5 | NA |
| 20 | 10A | Cotton side | 25 gsm/ 20 gsm | 1.79 | 18.3% | 1.39 | 4.77 | 2.57 | 4 | 1.66 |
| 21 | 10B | Cotton side | 25 gsm/ 20 gsm | 2.66 | 25.1% | 2.76 | 2.76 | 2.76 | 4 | 2.87 |
| 22 | None | None | 30 gsm/ 20 gsm | 0 | 0.0% | NA | NA | NA | 2 | NA |

Each bond pattern is indicated by referencing the number of the Figure that illustrates it (among FIGS. 10A-10H). The bond point area is the area of each individual bond point in the pattern. The percentage bonded area is the total area of the bond points divided by the total area covered by the pattern. $D_{MD}$ is the distance between adjacent bond points in the machine direction (MD). $D_{CD}$ is the distance between adjacent bond points in the cross direction (CD). $D_{AV}$ is the mean of $D_{MD}$ and $D_{CD}$. The Fuzz Score is measured as defined below in the Test Methods section. Lower values mean less fuzz. A/L is the fiber free-length parameter, determined as defined below in the Test Methods section.

It was found that nonwoven webs with a fiber free-length parameter of less than 2.90 mm had good fuzz scores (1 or 2). It is believed that a fuzz score of less than 3 is acceptable. Nonwoven webs with a higher fiber free-length parameter had poorer abrasion resistance—that is, they exhibited more fuzz after the abrasion test. Nonwoven webs with no pattern of bond points exhibited the worst abrasion resistance. Impressing the bond points into the cotton side (that is, the second side 126) was found to produce more fuzz than impressing the bond points into the ATB side (first side 124). Increased total percentage bond area correlates with reduced fuzz. However, there may be a trade-off between softness of the nonwoven and abrasion resistance, in this regard, in that nonwovens with a very high bonded area may tend to be stiffer (less soft).

Absorbent Articles

Figure 11:
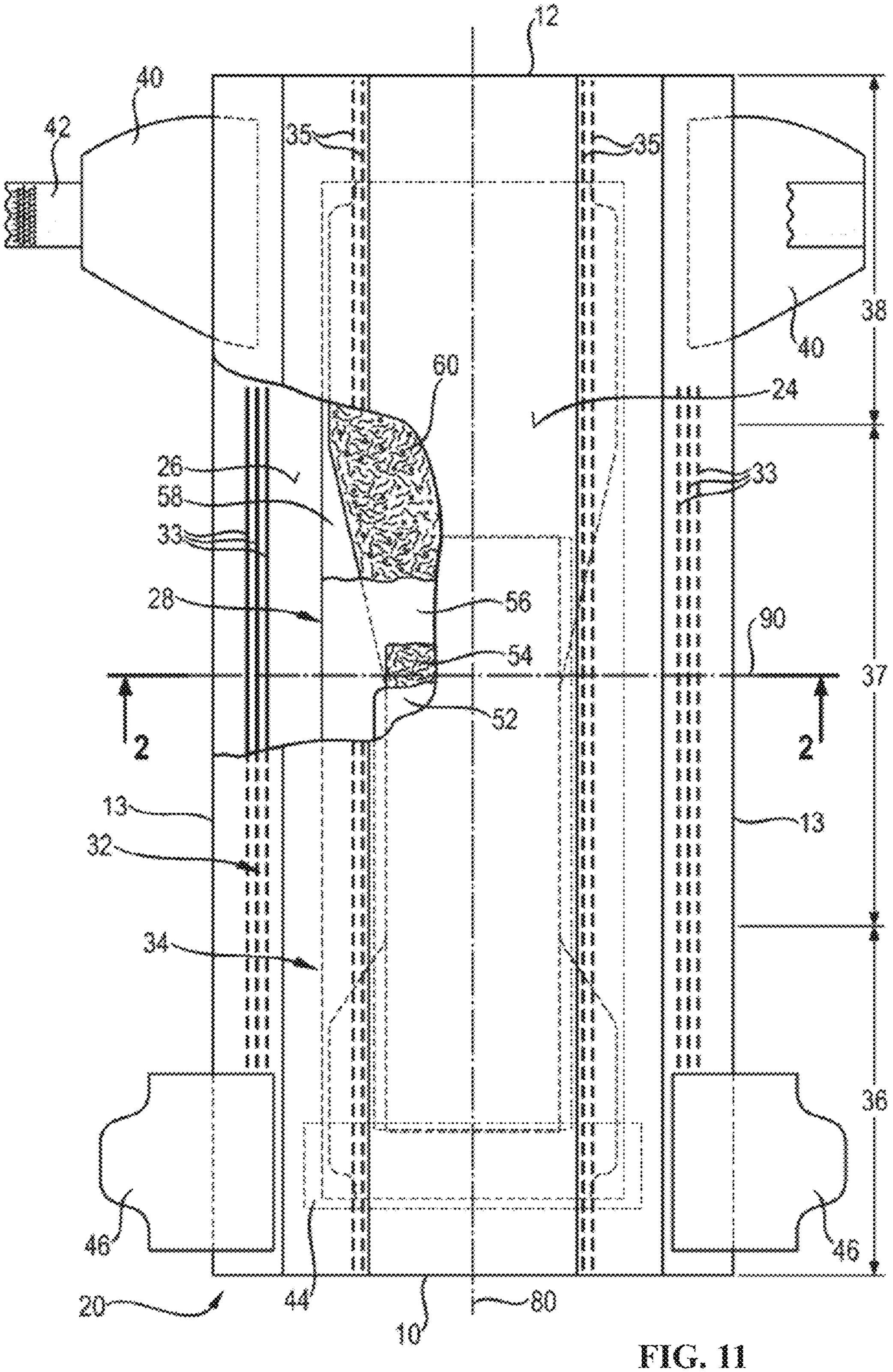
FIG. 11 is a schematic top plan view of a diaper.
Figure 12:
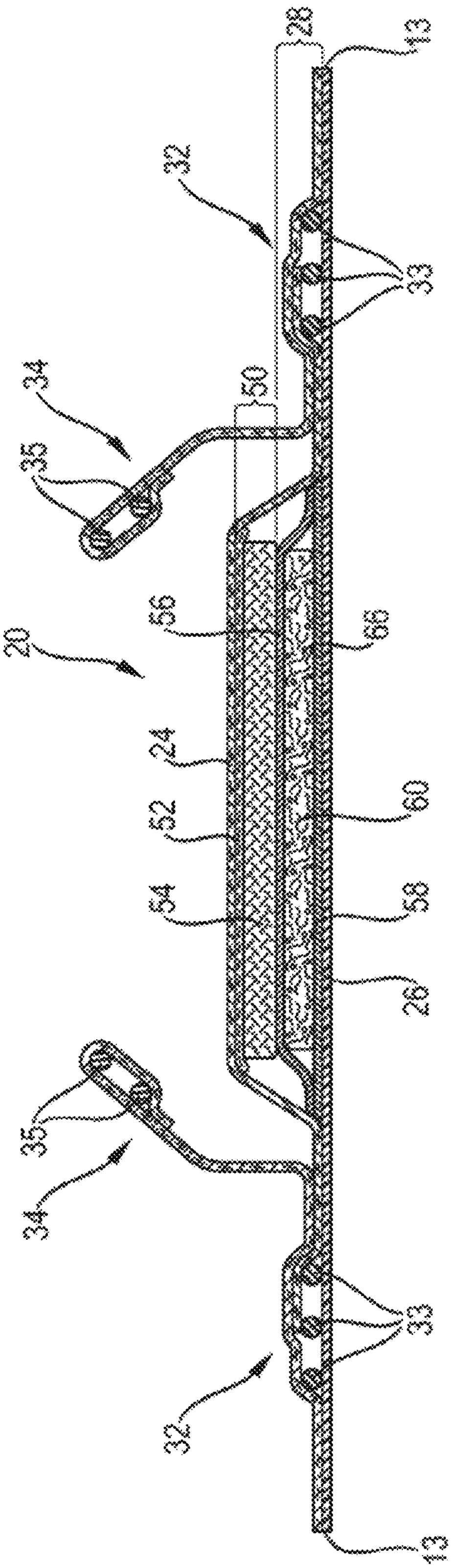
FIG. 12 is a schematic cross-sectional view of the diaper of FIG. 11, along the line 2-2.

Referring to FIGS. 11 and 12, an example absorbent article 20 is described. FIG. 11 is a top plan view of the absorbent article 20 (shown here: a diaper), in a flat-out state, with portions of the structure being cut-away to more clearly show the construction of the absorbent article 20. The absorbent article 20 is shown for illustrative purposes only as the present disclosure may be used for making a wide variety of diapers or other absorbent articles.

The absorbent article 20 comprises a liquid permeable topsheet 24, a liquid impermeable backsheet 26, an absorbent core 28 positioned intermediate the topsheet 24 and the backsheet 26, an optional acquisition layer 52 underneath the topsheet, and, optionally, a distribution layer 54 beneath the acquisition layer and above the absorbent core. The absorbent article 20 comprises a front waist edge 10 (in a pantiliner or sanitary napkin, this edge of the article would be referred to as a front edge instead of front waist edge, given the article is considerably smaller and not worn around the waist of the wearer), and a back waist edge 12 (in a pantiliner or sanitary napkin, this edge of the article would be referred to as a back edge instead of back waist edge, given the article is considerably smaller and not worn around the waist of the wearer), and two longitudinal side edges 13. The front waist edge 10 is the edge of the absorbent article 20 that is intended to be placed towards the front of the user when worn, and the rear waist edge 12 is the opposite edge. The absorbent article 20 has a longitudinal dimension and a lateral dimension and may be notionally divided by a longitudinal axis 80 extending from the front waist edge 10 to the back waist edge 12 of the absorbent article 20 and dividing the absorbent article 20 in two substantially symmetrical halves relative to the longitudinal axis, when viewing the absorbent article 20 from the wearer-facing side in a flat, laid out configuration, as e.g. illustrated in FIG. 11.

The absorbent article 20 may be divided by a lateral axis 90 into a front half and a back half of equal length measured along the longitudinal axis 80, when the absorbent article 20 is in a flat, laid-out state. The absorbent article's lateral axis 90 is perpendicular to the longitudinal axis 80 and is placed at half the longitudinal length of the absorbent article 20.

The longitudinal dimension of the absorbent article extends substantially parallel to the longitudinal axis 80 and the lateral dimension extends substantially parallel to the lateral axis 90. The absorbent article 20 may be notionally divided into a front region 36, a back region 38 and a crotch region 37 located between the front region 36 and the back region 38 of the absorbent article 20. Each of the front, back and crotch regions are ⅓ of the longitudinal dimension of the absorbent article 20.

Absorbent articles especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers. In the examples below, the ADS 50 comprises two layers: a distribution layer 54 and an acquisition layer 52 disposed between the absorbent core and the topsheet. The ADS maybe free of superabsorbent polymer.

The function of a distribution layer 54 is to spread the insulting fluid liquid over a larger surface within the article so that the absorbent capacity of the absorbent core can be more efficiently used. Distribution layers maybe made of a nonwoven material based on synthetic or cellulosic fibers and having a relatively low density. The distribution layer may typically have an average basis weight of from 30 g/m2 to 400 g/m2, in particular from 80 g/m2 to 300 g/m2.

The absorbent article 20 may further comprise an acquisition layer 52, which is provided directly beneath the topsheet and above the absorbent core (and, if present, above the distribution layer). The function of the acquisition layer 52 is to quickly acquire the fluid away from the topsheet so as to provide a good dryness for the wearer. The acquisition layer may typically be or comprise a non-woven material, for example a SMS or SMMS material, comprising a spunbonded, a melt-blown and a further spunbonded layer or alternatively a carded chemical-bonded nonwoven. The nonwoven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

A further acquisition layer may be used in addition to a first acquisition layer described above. For example a tissue layer maybe placed between the first acquisition layer and the distribution layer. The tissue may have enhanced capillarity distribution properties compared to the acquisition layer described above. The tissue and the first acquisition layer may be of the same size or maybe of different size, for example the tissue layer may extend further in the back of the absorbent article than the first acquisition layer. An example of hydrophilic tissue is a 13-15 gsm high wet strength made of cellulose fibers from supplier Havix.

The absorbent core 28 may comprise an absorbent material 60 that is a blend of cellulosic fibers (so called "airfelt") and superabsorbent polymers in particulate form encapsulated in one or more webs, see for example U.S. Pat. No. 5,151,092 to Buell. Alternatively, the absorbent core 28 may be free of airfelt, or substantially free of airfelt.

FIG. 11 also shows other typical diaper components such as a fastening system comprising fastening tabs 42 attached towards the back waist edge 12 of the absorbent article 20 and cooperating with a landing zone 44 towards the front waist edge 10 of the absorbent article 20. The absorbent article 20 may also comprise front ears 46 and back ears 40 as it is known in the art.

The absorbent article may comprise further optional other features such as leg cuffs 32 and/or barrier cuffs 34, front and/or back waist features such as front and/or elastic waistbands attached adjacent to the respective front and/or back waist edge of the absorbent article.

The topsheet 24, the backsheet 26, and the absorbent core 28 may be assembled in a variety of well known configurations, in particular by gluing or heat embossing. Exemplary diaper configurations are described generally in U.S. Pat. Nos. 3,860,003; 5,221,274; 5,554,145; 5,569,234; 5,580,411; and 6,004,306.

In an absorbent article according to an example, the topsheet 24 comprises or consists of a nonwoven web as described above, comprising spunlaced cotton and thermoplastic fibers, with a pattern of bond points. The body facing surface of the absorbent article preferably comprises the second surface of the nonwoven web, so that the side rich in cotton fibers faces the skin of the wearer. This can provide a soft surface, and the impression of softness to the wearer and/or caregiver. The benefit of this may be particularly prominent for the topsheet, since the topsheet may come into contact with particularly sensitive parts of the wearer's body.

Alternatively or in addition, a nonwoven web as described above may be used as part of the liquid impermeable backsheet 26, or as a cover over the garment facing surface of the liquid impermeable backsheet 26. When used in this way, the garment facing surface of the absorbent article preferably comprises the nonwoven web. In particular, the garment facing surface of the absorbent article preferably comprises the second surface of the nonwoven web. In this way, the side rich in cotton fibers is on the exposed outer surface of the absorbent article, and the side rich in thermoplastic fibers faces inwardly, towards the absorbent core 28. Again, providing the cotton-rich surface on an outer surface of the absorbent article can present a soft surface, and can give the impression of softness to the wearer and/or caregiver.

In still another alternative, the absorbent article may comprise a belt (not shown in FIGS. 11 and 12). The belt may comprise a nonwoven web as described above. The nonwoven web may form at least part of an outer surface of the belt. In particular, the second side 126 of the nonwoven web (that is, the cotton-rich side) may form at least part of the outer surface. The outer surface may be body facing or garment facing, or may include both a body facing surface and a garment facing surface.

The diaper 20 may comprise leg cuffs 32 which provide improved containment of liquids and other body exudates. Leg cuffs 32 may also be referred to as leg bands, side flaps, barrier cuffs, or elastic cuffs. Usually, each leg cuff will comprise one or more elastic strings 33, represented in exaggerated form on FIGS. 11 and 12, comprised in the diaper for example between the topsheet and backsheet in the area of the leg openings to provide an effective seal while the diaper is in use. It is also usual for the leg cuffs to comprise "stand-up" elasticized flaps (barrier leg cuffs 34) which improve the containment of the leg regions. The barrier leg cuffs 34 will usually also comprise one or more elastic strings 35, represented in exaggerated form in FIGS. 11 and 12.

The absorbent core 28 may comprise an absorbent material 60 enclosed within a core wrap 56 and 58. The absorbent material 60 may comprise from 80% to 100% of superabsorbent polymer (SAP) 66, such as SAP particles, by total weight of the absorbent material 60. The core wrap 56 and 58 is not considered as an absorbent material 60 for the purpose of assessing the percentage of SAP in the absorbent core 28.

The absorbent core 28 of the invention may comprise adhesive for example to help immobilizing the SAP 66 within the core wrap 56 and 58 and/or to ensure integrity of the core wrap, in particular when the core wrap is made of one or more substrates. The core wrap will typically extend over a larger area than strictly needed for containing the absorbent material 60 within.

The absorbent material 60 may be encapsulated in one or more substrates. The core wrap comprises a top side 56 facing the topsheet 24 and a bottom side 58 facing the backsheet 26, as shown in FIG. 12. The core wrap may be made of a single substrate folded around the absorbent material 60. The core wrap may be made of two substrates (one mainly providing the top side and the other mainly providing the bottom side) which are attached to another. Typical configurations are the so-called C-wrap and/or sandwich wrap.

The core wrap may be formed by any materials suitable for receiving and containing the absorbent material 60. The core wrap may in particular be formed by a nonwoven web, such as a carded nonwoven, spunbond nonwoven ("S") or meltblown nonwoven ("M"), and laminates of any of these.

Variants

Examples were described above of absorbent articles in which the topsheet and/or backsheet comprises a nonwoven web. Alternatively or in addition to either (or both) of these possibilities, another component of the absorbent article may comprise the nonwoven web. Examples of the other component include but are not limited to a belt.

Although the example was given above of a diaper, the nonwoven web may be used in other absorbent articles.

In all of the examples shown in FIGS. 10A-10H, the discrete bond points have identical size, shape, and orientation. This is not essential. In other examples, different bond points within a pattern may have different sizes, shapes, and/or orientations. Furthermore, the pattern of discrete bond points need not be a uniform lattice defined by a quadrilateral primitive cell.

In the examples described above, the bond points were impressed into the first side 124 of the nonwoven web by the pins of the pin roll, while the second side of the nonwoven web remained substantially smooth (flat). In some examples, the bond points may be impressed into both the first side 124 and the second side of the web—for example by providing two patterned calendar rolls, instead of one patterned roll and one smooth roll.

For the examples above, it was suggested that a hydrophobic wax may be applied to the nonwoven web. In other examples, other hydrophobic compounds may be applied, including but not limited to: a silicone polymer, a triglyceride, a diglyceride, a monoglyceride, a hydrocarbon, or a wax ester.

Test Methods

Fiber Free-Length (1) Sample Preparation

When a nonwoven is available in a raw material form, a rectangular specimen with a size of 100 mm×50 mm is cut from the raw material, where the long (100 mm) side of the rectangle is oriented along the material MD direction, and the short (50 mm) side is along the material CD direction When a nonwoven is a component of a finished product, the nonwoven is removed from the finished product using a razor blade to excise the nonwoven from other components of the finished product and cut to provide a nonwoven specimen with a size of 100 mm×50 mm, which is free from folds or wrinkles. The sample should be cut from the center of the article. That is, the sample is centered on the intersection of the longitudinal centreline and lateral centreline of the absorbent article. The longitudinal centreline of the sample is therefore aligned with the longitudinal centreline of the absorbent article, and the lateral centreline of the sample is aligned with the lateral centreline of the absorbent article. The long (100 mm) side of the rectangle is oriented parallel to the longitudinal centerline of the article. A cryogenic spray (such as Cyto-Freeze, Control Company, Houston Tex.) may be used to remove the nonwoven sample from other components of the finished product, if necessary.

(2) Image Generation and Fiber Free-Length

The side of the nonwoven into which the pattern of bond points is impressed is observed by a digital microscope. The field of view is set to obtain a digital image containing at least 4 adjacent bond points. The image should be captured at a spatial resolution to adequately capture the detailed shape of each bond point. The image analysis is performed subsequently by a commercial software tool, such as ImageJ 1.49v, National Institutes of Health, USA. The image is spatially calibrated such that each set of pixel coordinates in the image corresponds to a relative spatial position in the plane of the nonwoven imaged. A binary image is created manually in which each of the captured bond points is labeled as "1" and segmented from the surrounding background (labeled as "0"). Each labeled bond point should be a fully-filled shape with smooth outlines, to be as consistent as possible with the pattern of bond points. For each bond point, the set of coordinates ($x_i$, $y_i$) corresponding to that bond point is extracted using the image processing software. Based on the coordinates of all pixels in a given bond point, the centroid of the bond point ($x_0$, $y_0$) is calculated, as $$\left(x_0 = \frac{1}{n}\sum\nolimits_{i=1}^{n} x_i,\ y_0 = \frac{1}{n}\sum\nolimits_{i=1}^{n} y_i\right)$$

with n being the total number of pixels contained in the bond point. The unit conversion from length in pixels to length in millimeters is calculated by multiplying the dimension in pixels by the resolution ratio ($R_0$). The resolution ratio is determined by reading the millimeter value indicated on the resolution bar in the image, and dividing this by the measured length of the resolution bar in pixels.

Figure 13A:
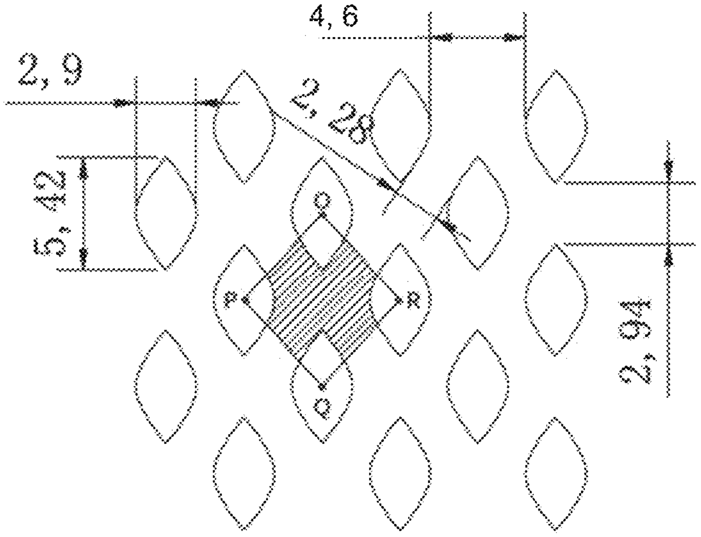
FIG. 13A is a schematic diagram showing part of a pattern of bond points and illustrating the calculation of a fiber free-length parameter.

Four adjacent bond points are selected, as illustrated in the example of FIG. 13A, and the four centroids, O, P, Q, R, of these four adjacent bond points are connected, to form a closed quadrilateral. This quadrilateral contains parts of each of the four bond points, as well as an area between the bond points. The area within the quadrilateral OPQR and between the bond points is denoted the "non-bonded area", indicating that it is not part of any bond point (although, of course, the individual fiber-to-fiber bonds between the thermoplastic fibers, imparted by through-air bonding, will typically still be present in this area). The non-bonded area, A, is determined by counting the number of pixels in the non-bonded area and converting to units of $mm^2$ according to the spatial resolution of the image, using the resolution ratio ($R_0$).

Figure 13B:
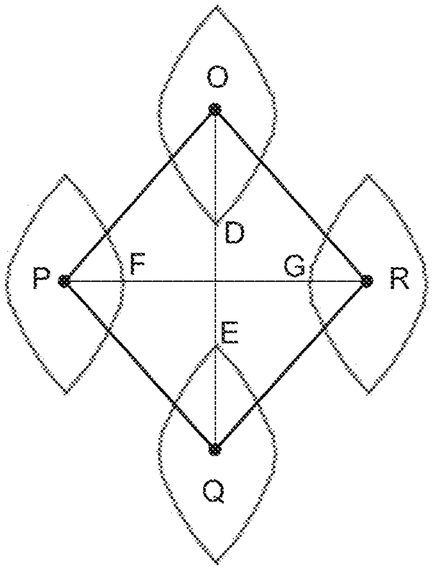
FIG. 13B is an enlarged version of part of the pattern in FIG. 13A.

Two lines are drawn, one connecting O and Q and the other connecting P and R. The line connecting O and Q is referred to as line OQ, and the line connecting P and R is referred to as line PR, as illustrated in the enlarged view of FIG. 13B. Next, the points where the lines OQ and PR cross the boundary of the non-bonded area are identified. Point D is the point where the line OQ crosses the boundary of the bond point containing O. Point E is the point where the line OQ crosses the boundary of the bond point containing Q. Likewise, point F is the point where the line PR crosses the boundary of the bond point containing P; and point G is the point where the line PR crosses the boundary of the bond point containing R. The distance between points D and E is denoted DE. The distance between points F and G is denoted FG. The longer of distances DE and FG is defined as length L.

The fiber free-length parameter is defined as the area A divided by the length L—that is, A/L. This parameter is reported in millimeters, to two decimal places.

Figure 13C:
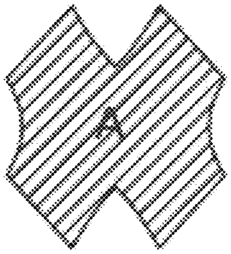
FIG. 13C shows a non-bonded area in the primitive cell of FIG. 13B.
Figure 14A:
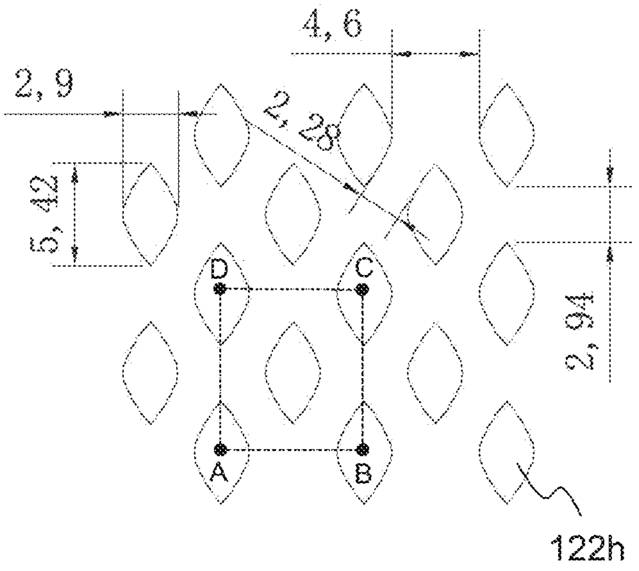
FIG. 14A illustrates an example of a non-primitive unit cell.
Figure 14B:
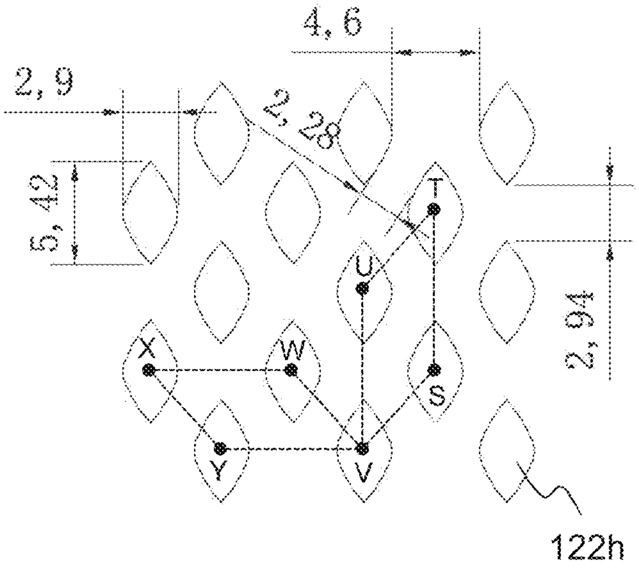
FIG. 14B illustrates primitive unit cells formed between bond points that are not nearest neighbors.

When the pattern of discrete bond points is a regular lattice pattern (like those in FIG. 10A-H), the quadrilateral used for calculating the fiber free-length is a primitive unit cell. It is formed by joining pairs of bond points that are nearest neighbors. In the example in FIG. 13, the primitive unit cell is a rhombus. For greater clarity, FIGS. 14A and 14B give some examples of incorrect selections of the quadrilateral. FIG. 14A shows a non-primitive unit cell ABCD in dashed outline. It is non-primitive because it encloses more than one bond point—specifically, it encloses an additional bond point in the middle of the unit cell. FIG. 14B shows two unit cells STUV and VWXY in dashed outline. Each of these is a primitive unit cell, in that each can be used to create the entire pattern by translation, in a tiled fashion, without gaps or overlaps, and each encloses exactly one bond point, in total. However, these primitive unit cells are formed by joining bond points that are not nearest neighbors. In particular, the lines WX, VY, UV and TS link bond points that are not nearest neighbors. Only the quadrilateral OPQR in FIG. 13 satisfies all of the requirements, and is the correct quadrilateral for calculating the fiber free-length. It can be seen that, when there is a choice of primitive unit cells in a 2-D lattice pattern, the correct primitive unit cell is the one with the shortest perimeter.

The fiber free-length parameter can also be calculated for patterns that are not defined by a regular lattice. Note that, if the pattern of discrete bond points does not follow a regular distribution, there could be several combinations of the 4 adjacent bond points to form the closed quadrilateral. In this case, values of A/L should be calculated for all of these quadrilaterals, and the maximum value of A/L is selected as the fiber free-length.

Without wishing to be bound by theory, it is believed that the fiber free-length parameter. A/L, is correlated with the shorter of two possible spans across a non-bonded area. This may explain why smaller values of this parameter correlate well with reduction in fuzz (that is, improved abrasion resistance.)

Abrasion Resistance (Fuzz)

Material fuzz performance is measured by the abrasion resistance method, which is to evaluate the morphology change of a nonwoven surface after 200 cycles of rubbing with a geometric figure under 2.9 KPa pressure.

The geometric figure is a Lissajous figure—in particular, a straight line, which becomes gradually a widening ellipse, until it forms another straight line in the opposite direction. The equations defining the Lissajous figure are as follows:

$$\begin{cases} x(\theta) = a\sin(p\theta) \\ y(\theta) = b\sin(q\theta + \phi) \\ 0 \leq \theta \leq 2\pi \end{cases}$$

where $\phi=0$, $a=b$, $p=9$ and $q=8$. The rubbing test is conducted by a Martindale instrument which follows the requirements in ASTM D4966-12. For the examples reported in Table 1, a Darong YG (B) 401T, 9 position Martindale abrasion and pilling tester was used.

Before the test, the nonwoven material is firstly cut into the proper size to fit the sample holder of the Martindale instrument. The nonwoven is tightly fixed on the sample holder without wrinkles, and its cotton-rich side (second side) faces the abrasion head. A silicone rubber sheet with the coefficient of friction in the range 0.48 to 0.56 is employed as the rubbing surface on the abrasion head. The rubbing speed is 25 rpm, and after 200 cycles of rubbing, the nonwoven material is removed from the sample holder for grading.

Figure 15A:
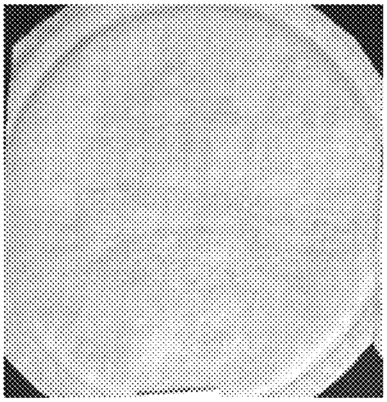
FIGS. 15A-C illustrate examples of different fuzz scores, according to the test method described herein.
Figure 15B:
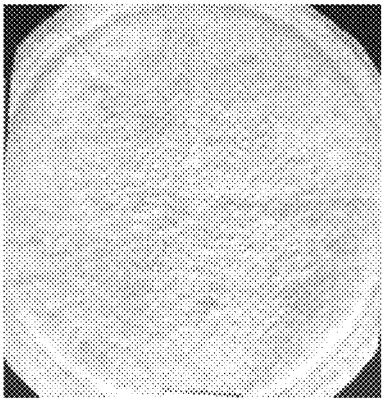

The grading rule is as follows:

Score-1: The nonwoven surface generates no free fibers or fiber pills (see FIG. 15A for an example);

Score-2: The nonwoven surface generates less than 10 fiber pills and the maximum dimension of each pill is smaller than 1 mm (see FIG. 15B for an example).

Score-3: The nonwoven surface generates 10 to 20 fiber pills, with the maximum dimension of each pill being smaller than 1 mm; or generates less than 10 fiber pills but at least one pill has a maximum dimension in the range 1 to 5 mm Score-4: The nonwoven surface generates more than 20 fiber pills; or generates fiber pills or clusters whose maximum dimension is bigger than 5 mm.

Figure 15C:

Score-5: The nonwoven surface is broken (see FIG. 15C for an example).

Thermogravimetric Analysis (TGA)

The following TGA method can be used determine the proportion of different types of fiber in a sample of nonwoven web. In particular, it is used for determining the basis weight of cellulosic (for example, cotton) fibers in the nonwoven web. It is also used for determining the relative concentrations of cellulosic fibers and thermoplastic fibers at each side of the web.

When a nonwoven is available in a raw material form, 0.0500 to 0.0600 g of the nonwoven material is weighed using a weighing balance with an accuracy of 0.0001 g. This initial weight is recorded as Wi.

When a nonwoven is a component of a finished product, the nonwoven is removed from the finished product using a razor blade and separated from other components of the finished product. A cryogenic spray (such as Cyto-Freeze, Control Company, Houston Tex.) may be used to remove the nonwoven sample from other components if necessary. Then, the nonwoven is soaked in Tetrahydrofuran for 12 hrs to dissolve all the product adhesives. After soaking, the nonwoven sample is dried in a fume hood for 24 hrs. After that, 0.0500 to 0.0600 g of the nonwoven material is weighed using a weighing balance with an accuracy of 0.0001 g. Again, this initial weight is recorded as Wi.

When the percentage of the cellulosic fibers in the nonwoven first surface is to be measured, the sample needs to be soaked in a liquid nitrogen for 2 minutes, and then stuck on a metal plate by a double-sided glue tape with its second surface facing up. A rotating blade is used to shave the sample from its second surface until the weight of the remaining part is 50%±10% of its original weight Wi. The weight of the remaining part is recorded as Wi'. (If the goal is to calculate the overall percentage of cellulosic fibers, then this shaving step is skipped.)

The TGA method is used to identify the percentage of cellulosic fibers in the sample. The instrument used is a TMA/SDTA 2+LN/600, made by Mettler Toledo, or its equivalent. The nonwoven sample is placed in the chamber, and the temperature is set to 350° C. The weight loss curve is monitored. When the weight loss curve becomes flat, stop the experiment, and record the total weight loss as WL.

If the whole sample was tested, the weight percentage of cellulosic fibers in the nonwoven sample is calculated as WL/Wi.

If a shaved sample was tested, the weight percentage of the cellulosic fibers in the nonwoven first surface is calculated as WL/Wi'. (It will be understood that the percentage of cellulosic fibers in the second surface can be determined by a similar procedure, but reversing the orientation of the sample during the shaving step.)

In each case, 6 repeated samples are tested to get the mean result.

Differential Scanning Calorimetry (DSC)

The following DSC method can be used to determine the presence of a number of thermoplastic components in the nonwoven. For example, it is used to determine whether the thermoplastic fibers are monocomponent or bicomponent fibers, or multicomponent fibers with more than two components.

When a nonwoven is available in a raw material form, 0.1000 to 0.2000 g of the nonwoven material is weighed using a weighing balance with an accuracy of 0.0001 g.

When a nonwoven is a component of a finished product, the nonwoven is removed from the finished product using a razor blade and separated from other components of the finished product. A cryogenic spray (such as Cyto-Freeze, Control Company, Houston Tex.) may be used to remove the nonwoven sample from other components if necessary. Then, the nonwoven is soaked in Tetrahydrofuran for 12 hrs to dissolve all the product adhesives. After soaking, the nonwoven sample is dried in a fume hood for 24 hrs. After that, 0.1000 to 0.2000 g of the nonwoven material is weighed using a weighing balance with an accuracy of 0.0001 g.

The DSC method is used to identify the melting point of a thermoplastic component. The instrument used is a DSC1, made by Mettler Toledo, or its equivalent. The nonwoven sample is placed in the chamber, and the temperature is scanned from 100 to 260° C. The speed of temperature increase is set to 5° C./min. The heat absorption curve is monitored. The temperature at which the curve has a local maximum (that is, a heat absorption peak) is recognized as the melting point of one of the thermoplastic components.

Mean Fiber Length of Cellulosic Fibers/Proportion of Short Cellulosic Fibers

The mean fiber length of a sample of cellulosic fibers (for example, cotton fibers) is measured as the mean length by weight of fibers. Likewise, the proportion of short fibers (those having a length of less than 12.7 mm) is determined as a proportion by weight of fibers. The test procedure is as follows:

- Step 1: Store the fibers at 25° C.+/−2° C., and 50%+/−10% Relative Humidity, for 24 hrs, to achieve equilibrium;
- Step 2: Measure a sample of 2.00 g+/−0.01 g of the fibers, using a weighing balance with an accuracy of 0.0001 g.
- Step 3: Feed the sample of fibers into an AFIS tester (available from Uster Technology AG, Switzerland) and generate the fiber length distribution report.

The mean length by weight of the fibers, and the percentage of fibers by weight having a length less than 12.7 mm, are obtained from the fiber length distribution report.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a topsheet;

a backsheet; and an absorbent core positioned between the topsheet and the backsheet;

wherein the absorbent article comprises a nonwoven web, the nonwoven web having a first side and a second side, the nonwoven web comprising thermoplastic fibers and cellulosic fibers;

wherein at least a portion of the thermoplastic fibers are present on the first side and at least a portion of the cellulosic fibers are present on the second side;

wherein a concentration of the thermoplastic fibers at the first side is higher than a concentration of the cellulosic fibers at the first side, and wherein a concentration of the thermoplastic fibers at the second side is less than a concentration of the cellulosic fibers at the second side;

wherein the nonwoven web has a pattern of discrete bond points, wherein the discrete bond points have a basis weight greater than zero;

wherein the pattern of discrete bond points has a fiber free-length parameter, as measured by the Free Fiber Length Test, with a value of less than 2.90 mm;

wherein the second side of the nonwoven web forms part of an exterior surface of the absorbent article; and wherein the discrete bond points are impressed into the first side of the nonwoven web.

2. The absorbent article of claim 1, wherein the nonwoven web is a spunlaced nonwoven web.

3. The absorbent article of claim 1, wherein the cellulosic fibers are cotton fibers.

4. The absorbent article of claim 1, wherein the cellulosic fibers have a mean fiber length of at least 20 mm, and wherein the mean fiber length is determined by weight of fibers according to the Mean Fiber Length of Cellulosic Fibers/Proportion of Short Cellulosic Fibers Test.

5. The absorbent article of claim 1, wherein the nonwoven web has a basis weight in the range of 25 gsm to 70 gsm.

6. The absorbent article of claim 1, wherein the cellulosic fibers are present in the nonwoven web at a basis weight in the range of 10 gsm to 50 gsm.

7. The absorbent article of claim 1, wherein the thermoplastic fibers are multicomponent fibers, comprising a first component and a second component, wherein the first component has a first melting point, wherein the second component has a second melting point, and wherein the first melting point is different from the second melting point.

8. The absorbent article of claim 7, wherein the first component is polyethylene.

9. The absorbent article of claim 1, wherein the pattern is a regular pattern based on a primitive cell that repeats uniformly over the nonwoven web.

10. The absorbent article of claim 9, wherein the primitive cell is defined by four lattice points, and wherein each lattice point is located at the centroid of a respective one of the discrete bond points.

11. The absorbent article of claim 1, wherein the discrete bond points have at least one of, or any combination of two or more of:

identical size;

identical shape; and identical orientation.

12. The absorbent article of claim 1, wherein a total area of the discrete bond points as a proportion of a total area of the nonwoven web is in the range of 5% to 50%.

13. The absorbent article of claim 1, wherein the nonwoven web forms at least a portion of the topsheet, and wherein the second side of the nonwoven web forms a body facing surface of the absorbent article.

14. The absorbent article of claim 1, wherein the nonwoven web forms at least a portion of the backsheet, and wherein the second side of the nonwoven web forms a garment facing surface of the absorbent article.

15. The absorbent article of claim 1, comprising a belt, wherein the nonwoven web forms at least a portion of the belt.

16. The absorbent article of claim 1, wherein the nonwoven web comprises apertures, projections, or recesses.

17. The absorbent article of claim 1, wherein the nonwoven web comprises projections and/or recesses.

18. The absorbent article of claim 1, wherein the nonwoven web is coated by a hydrophobic material.

19. An absorbent article comprising:

a topsheet;

a backsheet; and an absorbent core positioned between the topsheet and the backsheet;

wherein the absorbent article comprises a nonwoven web, the nonwoven web having a first side and a second side, the nonwoven web comprising thermoplastic fibers and cellulosic fibers;

wherein a concentration of the thermoplastic fibers at the first side is higher than a concentration of the cellulosic fibers at the first side, and wherein a concentration of the thermoplastic fibers at the second side is less than a concentration of the cellulosic fibers at the second side;

wherein at least a portion of the thermoplastic fibers are present on the first side and at least a portion of the cellulosic fibers are present on the second side;

wherein the nonwoven web has a pattern of discrete bond points;

wherein the discrete bond points comprise a fused mass of thermoplastic material that enrobes at least some of the cellulosic fibers;

wherein the pattern of discrete bond points has a fiber free-length parameter, as measured by the Free Fiber Length Test, with a value of less than 2.90 mm;

wherein the second side of the nonwoven web forms part of an exterior surface of the absorbent article; and wherein the discrete bond points are impressed into the first side of the nonwoven web.

20. An absorbent article comprising:

a topsheet;

a backsheet;

an absorbent core positioned between the topsheet and the backsheet; and a nonwoven web comprising a first side, a second side, thermoplastic fibers, and cellulosic fibers;

wherein at least a portion of the thermoplastic fibers are present on the first side and at least a portion of the cellulosic fibers are present on the second side;

wherein a concentration of the thermoplastic fibers at the first side is higher than a concentration of the cellulosic fibers at the first side, wherein a concentration of the thermoplastic fibers at the second side is less than a concentration of the cellulosic fibers at the second side, wherein at least a portion of the thermoplastic fibers are present on the second side, and wherein at least a portion of the cellulosic fibers are present on the first side;

wherein the nonwoven web has a pattern of discrete bond points;

wherein the pattern of discrete bond points has a fiber free-length parameter, as measured by the Free Fiber Length Test, with a value of less than 2.90 mm;

wherein the second side of the nonwoven web forms part of an exterior surface of the absorbent article; and wherein the discrete bond points are impressed into the first side of the nonwoven web.

* * * * *